US011708585B2

(12) United States Patent
Wu et al.

(10) Patent No.: US 11,708,585 B2
(45) Date of Patent: Jul. 25, 2023

(54) METHOD, SYSTEM AND RECOMBINANT BACMID FOR PREPARATION OF RECOMBINANT ADENO-ASSOCIATED VIRUS

(71) Applicant: Wuhan Institute of Physics and Mathematics, Chinese Academy of Sciences, Wuhan (CN)

(72) Inventors: Yang Wu, Wuhan (CN); Fuqiang Xu, Wuhan (CN); Ting Mei, Wuhan (CN); Liangyu Jiang, Wuhan (CN); Zengpeng Han, Wuhan (CN)

(73) Assignee: WUHAN INSTITUTE OF PHYSICS AND MATHEMATICS, CHINESE ACADEMY OF SCIENCES, Wuhan (CN)

( * ) Notice: Subject to any disclaimer, the term of this patent is extended or adjusted under 35 U.S.C. 154(b) by 476 days.

(21) Appl. No.: 16/455,745

(22) Filed: Jun. 28, 2019

(65) Prior Publication Data
US 2020/0208175 A1 Jul. 2, 2020

Related U.S. Application Data

(63) Continuation-in-part of application No. PCT/CN2019/080295, filed on Mar. 29, 2019.

(30) Foreign Application Priority Data

Dec. 28, 2018 (CN) ......................... 201811618542.X

(51) Int. Cl.
| | |
|---|---|
| *C12N 15/864* | (2006.01) |
| *C12N 15/866* | (2006.01) |
| *C12N 15/35* | (2006.01) |
| *C12N 7/00* | (2006.01) |
| *C12N 15/86* | (2006.01) |

(52) U.S. Cl.
CPC .... *C12N 15/86* (2013.01); *C12N 2710/10043* (2013.01); *C12N 2710/10052* (2013.01); *C12N 2710/14043* (2013.01)

(58) Field of Classification Search
None
See application file for complete search history.

(56) References Cited

U.S. PATENT DOCUMENTS 10,017,783 B2 * 7/2018 Galibert .................. C12N 7/00

FOREIGN PATENT DOCUMENTS

WO WO 2010055292 * 5/2010

OTHER PUBLICATIONS

Kaba et al., Development of a chitinase and v-cathepsin negative bacmid for improved integrity of secreted recombinant proteins, Journal of Virological Methods 122 (2004) 113-118.*
Aslanidi et al., An inducible system for highly efficient production of recombinant adeno-associated virus (rAAV) vectors in insect Sf9 cells, PNAS, 2009, pp. 5059-5064.*
Invitrogen, Bac-to-Bac® Baculovirus Expression System, 2015, pp. 1-80.*
Smith et al., A Simplified Baculovirus-AAV Expression Vector System Coupled With One-step Affinity Purification Yields High-titer rAAV Stocks From Insect Cells, Molecular Therapy, 2009, pp. 1888-1896.*

* cited by examiner

*Primary Examiner* — Maria Marvich
(74) *Attorney, Agent, or Firm* — Matthias Scholl P.C.; Matthias Scholl

(57) ABSTRACT

A method of preparing a recombinant adeno-associated virus (rAAV) including: (1) preparing a shuttle plasmid and a corresponding recombinant bacmid including a baculovirus genome, where the shuttle plasmid includes at least an rAAV gene of interest flanked by inverted terminal repeats (ITR-GOI) integrated with a heterologous functional gene fragment, and the recombinant bacmid includes an expression cassette of functional protein components necessary for assembly of the rAAV; (2) integrating the rAAV ITR-GOI and the expression cassette of functional protein components by using the shuttle plasmid and the recombinant bacmid, to yield a recombinant bacmid including a recombinant baculovirus genome; and (3) transfecting, with the recombinant bacmid, a host cell line.

6 Claims, 31 Drawing Sheets

Specification includes a Sequence Listing.

METHOD, SYSTEM AND RECOMBINANT BACMID FOR PREPARATION OF RECOMBINANT ADENO-ASSOCIATED VIRUS

CROSS-REFERENCE TO RELATED APPLICATIONS

This application is a continuation-in-part of International Patent Application No. PCT/CN2019/080295 with an international filing date of Mar. 29, 2019, designating the United States, now pending, and further claims foreign priority benefits to Chinese Patent Application No. 201811618542.X filed Dec. 28, 2018. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND

The disclosure relates to the field of gene therapy, and more particularly to a method, a system and a recombinant bacmid for preparation of a recombinant adeno-associated virus (rAAV).

Typically, there are three main methods for large-scale preparation of rAAV using baculovirus systems (Bac systems): a TwoBac system, a OneBac system dependent on a packaging cell line, and a shuttle plasmid-based OneBac system independent from a packaging cell line.

The main processes of preparation of rAAV using the TwoBac system are as follows: the AAV Rep gene and Cap gene are integrated with a baculovirus genome by the shuttle plasmid-mediated Tn7 transposition, and the rAAV core expression element (ITR-GOI, gene of interest flanked by AAV inverted terminal repeats) is integrated with another baculovirus genome by the shuttle plasmid-mediated Tn7 transposition. Thereafter, the above two recombinant baculovirus (BEVs) are transferred to host cells to produce rAAV.

The main processes of preparation of rAAV using a OneBac system dependent on packaging cell lines are as follows. Firstly, a packaging cell line that induces the expression of the Rep gene and the Cap gene is constructed. The packaging cell line contains the expression elements of the Rep gene and the Cap gene. The expression of the Rep gene and the Cap gene is regulated by a strong promoter PH that promotes the late gene expression of baculovirus. The hr2 enhancer sequence and the AAV Rep protein binding sequence are added to the upstream of the PH promoter. Thereafter, a BEV-(ITR-GOI) carrying the rAAV ITR-GOI is used to transfect the packaging cell line, and the Rep gene and Cap gene in the packaging cell line are induced to express, followed by the production of rAAV.

The main processes of preparation of rAAV using a shuttle plasmid-based OneBac system are as follows. The Cap gene, Rep gene and rAAV ITR-GOI are integrated into one shuttle plasmid. The rAAV packaging elements on the shuttle plasmid are transferred to a baculovirus genome by Tn7 transposition. Thereafter, the resulting BEV is used to transfect host cells to produce rAAV.

However, the two BEV of the TwoBac system are inefficient in co-infecting cells and the productivity of each cell cannot be fully utilized. The infection is arbitrary and tends to produce rAAV particles with empty shells containing no nucleic acids. The preparation process is complex, and the quality of prepared rAAV is unstable.

With regard to the OneBac system dependent on a packaging cell line, the packaging cell line that induces the expression of the Rep gene and the Cap gene is difficult to construct and select. The preparation of rAAVs of different serotypes requires different packaging cell lines that can express the Cap gene of the corresponding serotypes. Thus, the method has poor flexibility and universality.

With regard to the shuttle plasmid-based One Bac system, the shuttle plasmid carrying the Cap gene, the Rep gene, and the ITR-GOI is difficult to construct. The preparation of different serotypes of rAAV requires a shuttle plasmid of the corresponding serotype. This is costly.

SUMMARY

The disclosure provides a method, a system and a recombinant bacmid for preparation of a rAAV. The rAAV ITR-GOI carrying a heterologous functional gene fragment is integrated with a shuttle plasmid. The expression cassettes of functional proteins necessary for assembly of rAAV are included in the shuttle plasmid and baculovirus genome, which reduces the difficulty of construction of the shuttle plasmids and improves the stability, compatibility and flexibility of the preparation system of the gene therapy vector.

The disclosure provides a method of preparing rAAV, the method comprising:

(1) Preparing a shuttle plasmid and a corresponding recombinant bacmid comprising a baculovirus genome.

The shuttle plasmid comprises at least a rAAV ITR-GOI integrated with a heterologous functional gene fragment.

The recombinant bacmid comprising the baculovirus genome comprises the other expression cassette of functional protein components necessary for assembly of the rAAV.

(2) Integrating the rAAV ITR-GOI and the expression cassette of functional protein components by using the shuttle plasmid and the recombinant bacmid obtained in (1), to yield a recombinant bacmid comprising the genome of the BEV used for preparing rAAV.

(3) Transfecting, with the recombinant bacmid obtained in (2), a host cell line for culture.

The recombinant bacmid in (1) comprises a baculovirus genome in which Chia gene and/or Cath gene are absent.

The expression cassette is inserted into loci of one or more non-essential genes of the recombinant bacmid the non-essential genes being selected from Chia (105, 353 bp-107, 008 bp), Cath (107, 054 bp-108, 025 bp), Ac124 (103, 864 bp-104,607 bp), p10 (118,911 bp-119,915 bp), p26 (118,116 bp-118,838 bp), p74 (119,207 bp-121,144 bp), ctx (2085 bp-2246 bp), egt (11,427 bp-12,947 bp), 39 k (29,371 bp-30,198 bp), orf51 (43,312 bp-44,268 bp), gp37 (51,417 bp-52,325 bp), iap2 (61,150 bp-61,899 bp) and odv-e56 (129,080 bp-130,210 bp).

The expression cassette is inserted into the loci of the non-essential gene Chia and/or Cath of the recombinant bacmid.

The preparation of the recombinant bacmid in (1) comprises inserting the expression cassette into a locus of a non-essential gene of the baculovirus genome by Red recombination.

The shuttle plasmid is based on the pfast.Bac.Dual (pFBD) plasmid, which comprises the expression cassette of the Rep gene or Cap gene of AAV.

The recombinant bacmid is derived from the genome of baculovirus AcMNPV, and comprises at least the expression cassette of the Cap gene and/or Rep gene of AAV. The expression cassette is located downstream of and regulated by the P10 or PH promoter.

The disclosure provides a preparation system of rAAV, which comprises a shuttle plasmid and a corresponding recombinant bacmid comprising a baculovirus genome.

The shuttle plasmid comprises at least a rAAV ITR-GOI integrated with a heterologous functional gene fragment.

The recombinant bacmid comprising the baculovirus genome comprises the other expression cassette of functional protein components necessary for assembly of the rAAV.

The recombinant bacmid comprises a baculovirus genome in which Chia gene and/or Cath gene are absent.

The expression cassette is inserted into loci of one or more non-essential genes of the recombinant bacmid, the non-essential genes being selected from Chia, Cath, Ac124, p10, p26, p74, ctx, egt, 39k, orf51, gp37, iap2, odv-e56.

The expression cassette is inserted into the loci of the non-essential gene Chia and/or Cath of the recombinant bacmid.

The shuttle plasmid is based on the pFBD plasmid, which comprises the expression cassette of the Rep gene or Cap gene of AAV.

The recombinant bacmid is derived from the genome of baculovirus AcMNPV, which comprises at least the expression cassette of the Cap gene and/or Rep gene from AAV. This expression cassette is located downstream of and regulated by the P10 or PH promoter.

The disclosure provides a recombinant bacmid for preparation of rAAV. The recombinant bacmid comprises at least one expression cassette of functional protein components necessary for assembly of the rAAV. The expression cassette is inserted into loci of one or more non-essential genes of the recombinant bacmid, the non-essential genes being selected from Chia, Cath, Ac124, pi 0, p26, p74, ctx, egt, 39k, orf51, gp37, iap2, odv-e56.

The recombinant bacmid comprises a baculovirus genome in which Chia gene and/or Cath gene are absent.

The expression cassette is inserted into the loci of the non-essential gene Chia and/or Cath of the recombinant bacmid.

The recombinant bacmid is derived from the genome of baculovirus AcMNPV.

This expression cassette is located downstream of and regulated by the P10 or PH promoter.

Advantages of the invention are summarized below.

The rAAV ITR-GOI and expression cassette of functional protein components necessary for assembly of the rAAV are carried by the shuttle plasmid and the recombinant bacmid, respectively. The preparation method is flexible and compatible. When preparing different rAAVs carrying a heterologous functional gene fragment, it is only necessary to construct a shuttle plasmid containing a corresponding ITR-GOI rather than constructing a plurality of shuttle plasmids. In addition, the genetic stability of the BEV comprising the baculovirus genome is improved. The preparation method is compatible with the existing Bac systems for the production of rAAV.

BRIEF DESCRIPTION OF DRAWINGS

FIG. 1A is a schematic diagram showing the distribution of rAAV packaging elements in the pFBD shuttle plasmid and AcMNPV recombinant bacmid; FIG. 1B is a schematic diagram showing the main packaging components of rAAV; FIG. 1C is a schematic diagram showing the structure of the pFBD shuttle plasmid; FIG. 1D is a schematic diagram showing the AcMNPV recombinant bacmid and its major non-essential loci. The double-stranded circular DNA of the AcMNPV genome of baculovirus has a full length 133,966 bp, and the sequence and map thereof refer to Maghodia et al, 2014, Genome Announc., 2(6): e01202-14. The structure of AcMNPV Bacmid (bMON14272) refers to Luckow et al, J Virol, 1993. 67(8): 4566-79.

FIG. 2A is a schematic diagram showing the construction of recombinant bacmid Bac-Tn7-(ITR-GOI)-Cap-Δ(Chia-Cath)-Rep; FIG. 2B is a micrograph showing the activity assay after Sf9 cells are infected with BEV; FIG. 2C is a micrograph showing the activity assay after HEK293 cells are infected with purified rAAV; FIG. 2D is a micrograph showing the purified rAAV virions detected by electron microscopy.

FIG. 3A is a schematic diagram showing the construction of recombinant bacmid Bac-Tn7-(ITR-GOI)-Rep-Δ(Chia-Cath)-Cap; FIG. 3B is a micrograph showing the activity assay after Sf9 cells are infected with BEV; FIG. 3C is a micrograph showing the activity assay after HEK293 cells are infected with purified rAAV; FIG. 3D is a micrograph showing the purified rAAV virions detected by electron microscopy.

FIG. 4A is a schematic diagram showing the construction of recombinant bacmid Bac-Tn7-(ITR-GOI)-Δ(Chia-Cath)-Rep-Cap; FIG. 4B is a micrograph showing the activity assay after Sf9 cells are infected with BEV; FIG. 4C is a micrograph showing the activity assay after HEK293 cells are infected with purified rAAV; FIG. 4D is a micrograph showing the purified rAAV virions detected by electron microscopy.

FIG. 5A is a schematic diagram showing the construction of recombinant bacmid Bac-Tn7-(ITR-GOI)-Δ(Chia-Cath)-Rep-ΔAc124-Cap; FIG. 5B is a micrograph showing the activity assay after Sf9 cells are infected with BEV; FIG. 5C is a micrograph showing the activity assay after HEK293 cells are infected with purified rAAV; FIG. 5D is a micrograph showing the purified rAAV virions detected by electron microscopy.

FIG. 6A is a schematic diagram showing the construction of recombinant bacmid Bac-Tn7-(ITR-GOI)-Δ(Chia-Cath)-Cap-ΔAc124-Rep; FIG. 6B is a micrograph showing the activity assay after Sf9 cells are infected with BEV; FIG. 6C is a micrograph showing the activity assay after HEK293 cells are infected with purified rAAV; FIG. 6D is a micrograph showing the purified rAAV virions detected by electron microscopy.

FIG. 8A is a diagram of Western blotting analysis showing the stability of the BEV-Tn7-(ITR-GOI)-Cap2-Rep2, which is OneBac system based on a shuttle plasmid (Yang et al., 2018, Mol Ther Methods Clin Dev. 2018 Jul. 4; 10:38-47); FIG. 8B shows the stability of the BEV in Example 1. FIG. 8C shows the stability of the BEV in Example 2. FIG. 8D shows the stability of the BEV in Example 3. FIG. 8E shows the stability of the BEV in Example 4. FIG. 8F shows the stability of the BEV in Example 5.

DETAILED DESCRIPTION

Figure 1A:
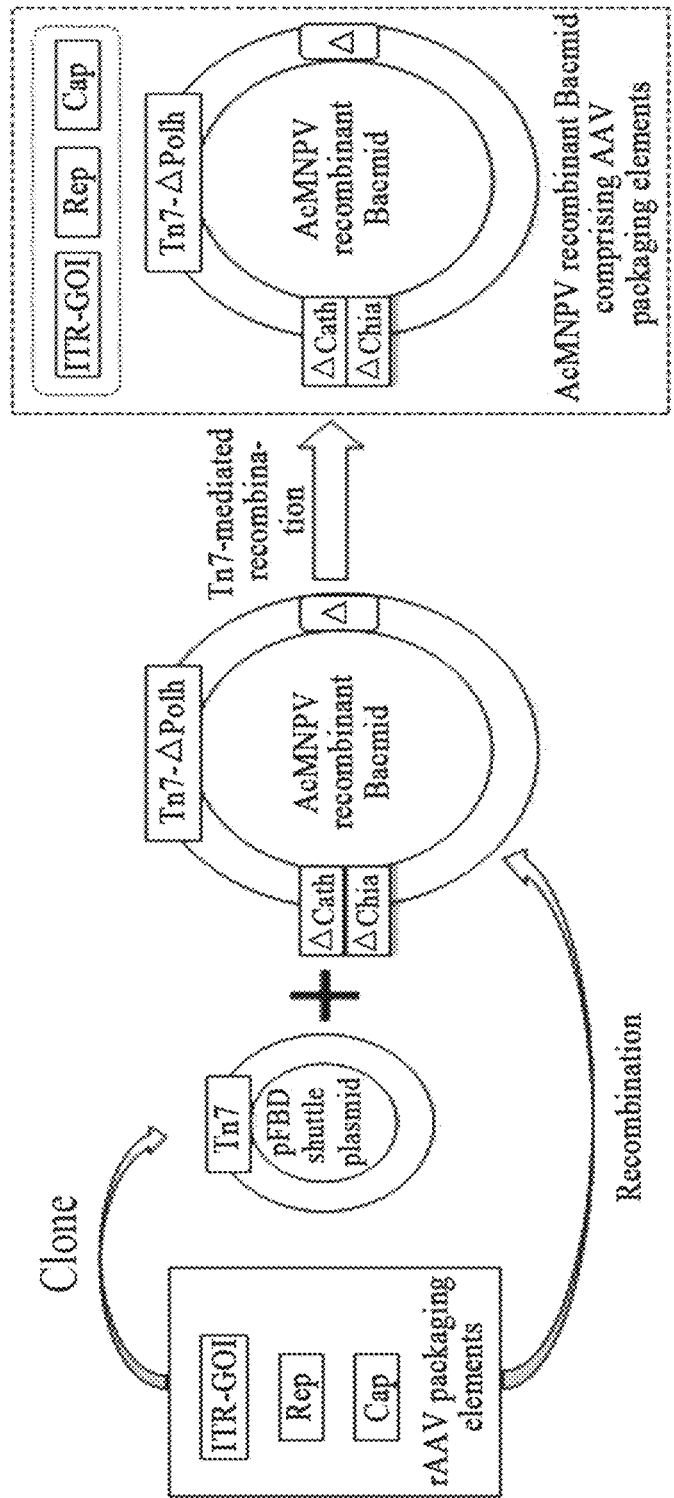
FIGS. 1A-1D are schematic diagrams of a Bac system for preparation of rAAV in the disclosure.
Figure 1B:
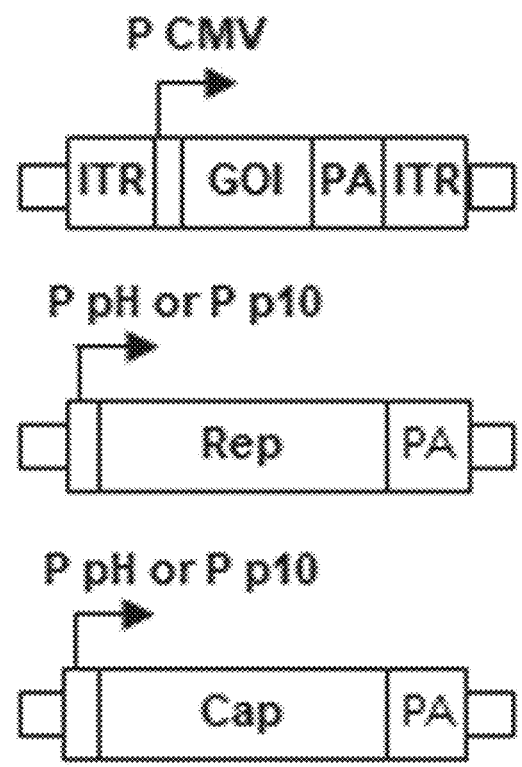
Figure 1C:
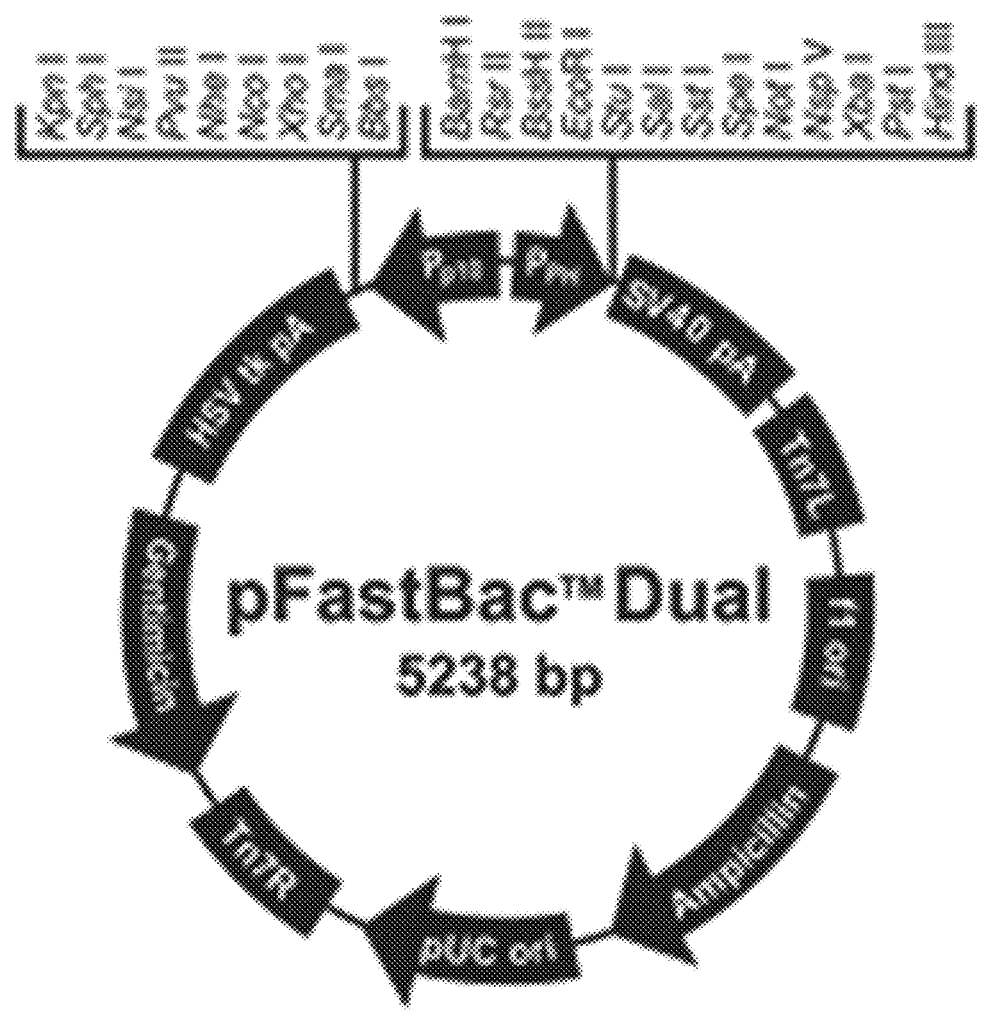
Figure 1D:
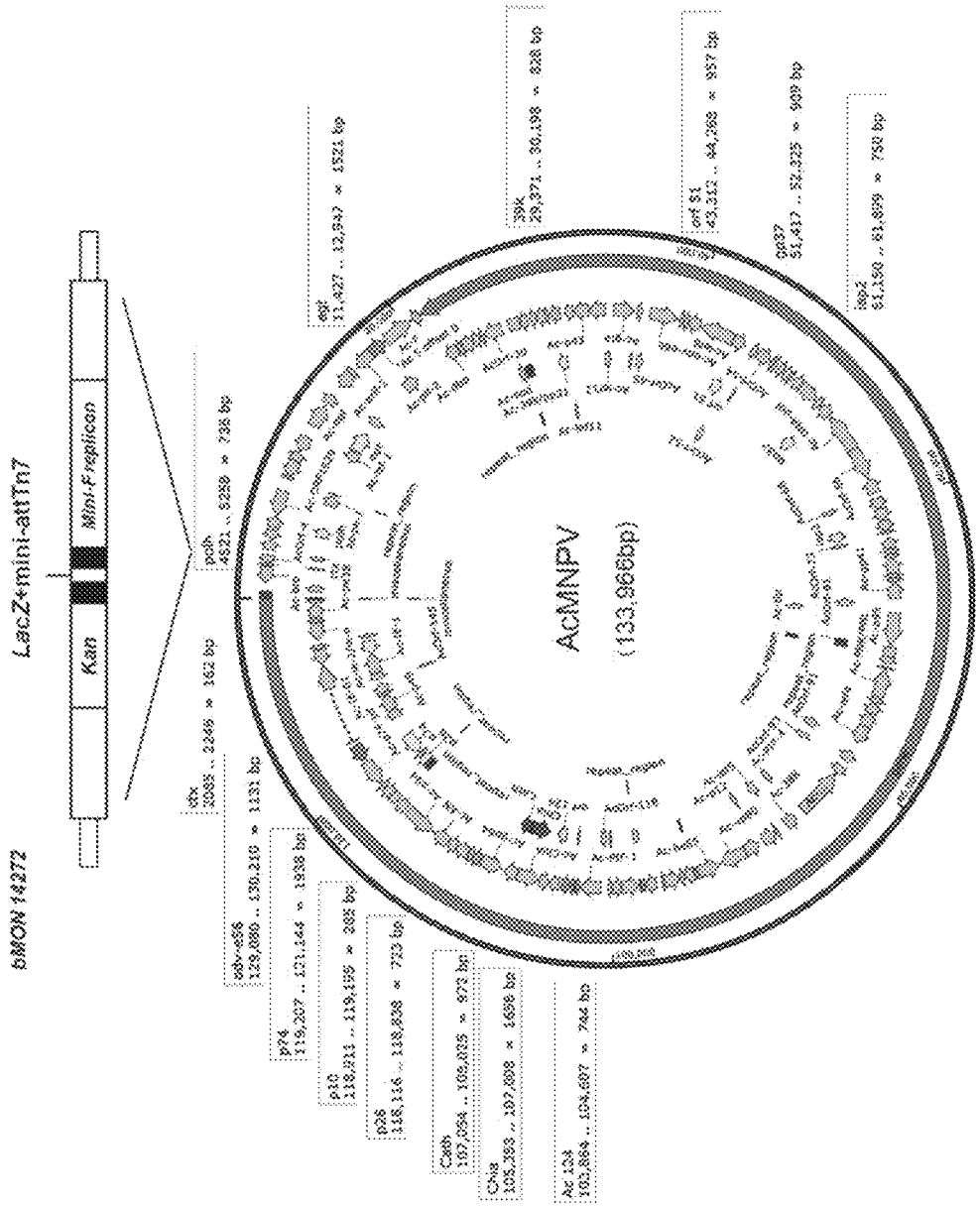

To further illustrate, experiments detailing a method, a system and a recombinant bacmid for preparation of a rAAV are described below. It should be noted that the following examples are intended to describe and not to limit the description.

The preparation method of the rAAV comprises the following steps:

(1) Preparing a shuttle plasmid and a corresponding recombinant bacmid comprising a baculovirus genome;

The shuttle plasmid comprises at least a rAAV ITR-GOI integrated with a heterologous functional gene fragment;

The shuttle plasmid is preferably a pFBD plasmid comprising at least a rAAV ITR-GOI integrated with a heterologous functional gene fragment. Alternatively, the pFBD plasmid may also comprise part of expression cassettes for producing functional protein components of rAAV. The expression cassette can be an expression cassette of the AAV functional protein components or other functional protein components.

The recombinant bacmid comprises other functional protein components necessary for the assembly of rAAV.

The expression cassette of the AAV, including the Rep gene and the Cap gene, can be loaded on the recombinant bacmid comprising the baculovirus genome. Thus, the shuttle plasmid comprises only the rAAV ITR-GOI carrying a heterologous functional gene fragment. For different heterologous functional gene fragments, it is only necessary to construct them into a shuttle plasmid to match the corresponding recombinant bacmid comprising the baculovirus genome. The type of recombinant bacmid is only related to the type of AAV functional protein component. In another aspect, the OneBac system implemented by the disclosure, unlike the OneBac system dependent on a packaging cell line, does not rely on a packaging cell line; compared to the OneBac system based on a shuttle plasmid, the stability, universality and compatibility of the BEV in the disclosure are greatly improved, and the load on the shuttle plasmid is greatly reduced.

In conventional Bac systems that prepare rAAV, the BEV carrying a foreign gene (AAV Rep gene, Cap gene or ITR-GOI) is inserted into a polyhedron (polh) genetic site of a non-essential gene in the baculovirus. Inserting into the polh genetic site tends to yield high levels of expression. To facilitate the construction of BEV, a commercial Bac-to-Bac system is utilized. The principle of the Bac-to-Bac system is detailed below. First, the exogenous DNA is transferred to the shuttle plasmid, and then the recombinant shuttle plasmid is transformed into *E. coli* containing the recombinant bacmid. The entire transformation process is mediated by the transposon Tn7 at the bacterial level. The recombinant bacmid DNA extracted from the above *E. coli* is used to transfect insect cells, and the BEV carrying the foreign gene is isolated therefore. The bacmid in this system is a macro-molecular circular DNA that can replicate and proliferate in both *E. coli* and insect cells and can produce BEV. The bacmid carry a bacterial origin of replication, an antibiotic resistance gene, a BEV genome, and a Tn7 recombinant cloning site. The earliest developer of the system, Luckow et al., used the polyhedron gene (polh) locus as a Tn7 recombinant cloning site (Luckow et al., 1993, *J. Virol.* 67 (8): 4566-4579).

Although multiple exogenous DNA sequences can be simultaneously inserted in a single site, this may cause the instability of the viral genome, which limits the insertion of certain types and number of exogenous DNAs. Thus, it is necessary to explore new sites suitable for inserting the rAAV packaging elements.

The loci of various non-essential genes that allow high expression of heterologous genes have been identified in the baculovirus genome. For example, Noad et al. found loci of non-essential genes ctx, egt, 39k, orf51, pg37, iap2, odv-e56 (Noad et al, 2009. BMC Molecular Biology 10:87), Kaba et al. showed that the stability of intracellular and secreted recombinant proteins is enhanced by knocking out the chitinase (Chia) gene and the cathepsin (Cath) gene (Kala et al., 2004, Journal of Virological Methods, 122, 113). -118). Hitchman et al. have shown that the expression level of foreign proteins increases due to the deletion of Chitinase, Cathepsin, P10, P26 and P74 genes (Hitchman et al, 2009, Cell BiolToxicol, 26: 57-68). Liang et al. showed that knocking out the Ac124 gene had no significant effect on the proliferation of AcMNPV (Liang et al., 2015, Arch Virol, 160(1): 275-84).

However, none of the above studies indicate whether the deletion or replacement of the non-essential loci of these baculoviruses is effective in the preparation of multi-protein complexes, rAAV or other recombinant viral vectors. Considering the complexity of rAAV and its difficulties in preparation, it is necessary to experimentally verify whether these loci can load the expression cassette of the AAV functional protein components.

The experimental results of the disclosure show that the expression cassettes of the AAV Rep and Cap genes necessary for the assembly of rAAV can be successfully loaded and expressed at the locus on the non-essential genes, such as Chia, Cath, Ac124, p10, p26, p74, ctx, egt, 39k, orf51, gp37, iap2 and odv-e56. The AAV Rep and Cap gene expression cassettes can be integrated into the recombinant bacmid, and the expression cassette is inserted into the locus of one or more non-essential genes of the recombinant bacmid, such as Chia, Cath, Ac124, p10, p26, p74, ctx, egt, 39k, orf51, gp37, iap2, odv-e56. Based on the recombinant bacmid described above, the shuttle plasmid pFBD-(ITR-GOI) carrying the rAAV ITR-GOI is recombined by transposon Tn7 to obtain a BEV genome integrating all rAAV packaging elements. The advantage is that it is compatible with existing ThreeBac, TwoBac, and OneBac systems that rely on Sf9/Rep-Cap packaging cell lines. The universal shuttle plasmid pFBD-(ITR-GOI) is directly recombined with the recombinant bacmid containing the expression cassette of Rep and Cap gene to obtain a novel BEV capable of producing rAAV. Compared with the OneBac system based on a shuttle plasmid, this scheme reduces the difficulty of constructing the shuttle plasmid and increases the spatial separation between the ITR-GOI and the expression cassettes of Rep and Cap genes. The stability of the new Bac system and the BEV are improved.

The recombinant bacmid corresponding to the shuttle plasmid comprises a baculovirus genome in which the non-essential gene Chia gene and/or Cath gene are deleted. The expression cassette of the functional protein component required for production of rAAV is inserted into the locus of one or more non-essential genes of the recombinant bacmid, such as Chia, Cath, Ac124, p10, p26, p74, ctx, egt, 39k, orf51, gp37, iap2, odv-e56.

Specifically, the expression cassette of the functional protein component required for production of rAAV is inserted into the locus of the non-essential gene Chia and/or Cath of the baculovirus.

The experiment shows that the deletion of Chia and Cath genes improves the stability of rAAV functional proteins. The Chia and Cath genes are protease genes, and are non-essential genes during the replication and assembly of the AcMNPV in Sf9 cells. This study found that these two genes have no negative effects on the production of rAAV virus.

The Chia gene and Cath gene are two adjacent genes. Using the method of homologous recombination, the Cath and Chia genes can be deleted while inserting the expression cassette of the AAV Rep and/or Cap genes. Therefore, the Cath and Chia genes loci can be used for insertion, and the Cath and Chia loci are also preferred as insertion sites.

The method for preparing the above BEV is as follows.

Using Red recombination technology, the gene fragment at the non-essential locus is replaced with an expression cassette containing the functional protein components necessary for assembly of the rAAV.

Recombination mediated by the transposon Tn7 is a fast and efficient method for inserting foreign genes into the BEV genome, but this method has limitations. The specific gene sequence needs to be inserted to recognize the transposon Tn7 in the BEV genome. The recombination cannot be performed at multiple different sites simultaneously or repeatedly. The transformation of the BEV genome remains complex and cumbersome.

Red recombination is a highly efficient recombinant method at the bacterial level. This method can be used to rapidly transform the BEV genome. Red recombination is a homologous recombination of a linear DNA fragment introduced into a cell with a specific target sequence of the genome, using a lambda phage Red recombinase (composed of three proteins, Exo, Beta, and Gam). The replacement of the gene of interest is finally achieved (Doublet et al., 2008, J Microbiol Methods., 75(2): 359-61).

The structure of the recombinant bacmid is referred to AcMNPV E2 (genomic sequences such as: Genbank accession No. KM667940.1) and AcMNPV Bacmid (bMON14272) from the references (Luckow et al, J Virol, 1993. 67(8): 4566-79). The expression cassette of the functional protein component necessary for the assembly of rAAV is located downstream of and regulated by the P10 or PH promoter.

The packaging of rAAV mainly involves three main components: the rAAV genome ITR-GOI, the Rep functional gene of AAV, and the Cap functional gene of AAV. In addition, other functional protein components such as AAP are also included, and the AAP gene has a certain promoting effect on increasing packaging efficiency.

With regard to the method for preparing rAAV of the disclosure, the rAAV ITR-GOI and the expression cassette of the functional protein components are respectively carried by a shuttle plasmid and a recombinant bacmid. This reduces the loading pressure of the shuttle plasmid carrying the heterologous gene fragments, and improves the stability of the BEV and the compatibility and flexibility of the AAV production system.

When the expression cassette of the functional protein components is the Cap gene with different serotypes the preparation method of the disclosure can reduce the complexity of the shuttle plasmid and the corresponding baculovirus. Specifically, when rAAV is prepared, the Rep gene expression cassette and the Cap gene expression cassette are required. The type 2 Rep gene is usually used to prepare rAAV of different serotypes. However, for the Cap gene that determines the extent of AAV infection and target specificity, it is necessary to select the Cap gene of a specific serotype. How many AAV serotypes there are, and how many specific serotypes of the Cap gene are needed. Up to now, more than 100 AAV serotypes and mutants have been developed. The existing OneBac system based on a shuttle plasmid contained both the Rep gene and Cap gene. For gene fragments with specific heterologous functionality, a variety of different shuttle plasmids are required to produce BEV with different types of AAV serotypes. This increases the difficulty of construction. The shuttle plasmid genome is small and hardly accommodates the Rep gene, Cap gene and ITR-GOI, resulting in poor stability of the shuttle plasmid. Studies have shown that the above integrated BEV can only stably pass on for 4 generations, and the yield of rAAV is significantly reduced in the fifth generations' BEV (refer to Yang et al., 2018, Mol Ther Methods Clin Dev. 2018 Jul. 4, 10:38-47).

In a technical solution, the shuttle plasmid contains both ITR-GOI and the expression cassette of Cap gene (pFBD-Cap-(ITR-GOI)), and the corresponding recombinant bacmid is integrated with the expression cassette of the Rep gene and the expression cassette of other functional protein components. Various ITR-GOIs can be flexibly matched with the Cap genes of various serotypes and combined on the pFBD shuttle plasmid. The preparation of rAAV requires only one recombinant bacmid incorporating the expression cassette of the Rep2 gene to satisfy different serotypes and carry different heterologous functional gene fragments. Compared with the OneBac system based on shuttle plasmid, this scheme maintains the flexibility of the OneBac system based on shuttle plasmid, reduces the difficulty of constructing the shuttle plasmid and increases the spatial separation between the ITR-GOI and the expression cassettes of Rep and Cap genes. The stability of the new Bac system and BEV has both been improved.

In another technical solution, when the shuttle plasmid contains both ITR-GOI and the expression cassette of Rep gene (pFBD-Rep-(ITR-GOI)), the corresponding recombinant bacmid is integrated with the expression cassette of the Cap gene and the expression cassette of other functional protein components. The preparation of rAAV requires a plurality of recombinant bacmids incorporating the expression cassettes of different serotype Cap genes to satisfy different serotypes and carry different heterologous functional gene fragments. Compared with the OneBac system based on shuttle plasmid, this scheme reduces the difficulty of constructing the shuttle plasmid and increases the spatial separation between the ITR-GOI and the expression cassettes of Rep gene. The stability of the new Bac system and BEV has both been improved. However, the flexibility of the system is reduced.

In still another technical solution, when the shuttle plasmid contains only ITR-GOI, the corresponding recombinant bacmid is integrated with the expression cassettes of the Rep and Cap genes and the expression cassette of other functional protein components. The preparation of rAAV requires a plurality of recombinant bacmids incorporating the expression cassette of the Rep2 gene and the corresponding expression cassette of many different serotype Cap genes to satisfy different serotypes and carry different heterologous functional gene fragments. Compared with the One Bac system based on shuttle plasmid, this scheme reduces the difficulty of constructing the shuttle plasmid and increases the spatial separation between the ITR-GOI and the expression cassettes of Rep and Cap genes. The stability of the new Bac system and BEV has both been improved. In addition, the system can be compatible with the shuttle plasmid pFBD-(ITR-GOI) of existing Bac systems.

(2) The rAAV ITR-GOI carrying the heterologous functional gene fragment is integrated with the expression cassettes of the functional protein components by using the shuttle plasmid and the recombinant bacmid obtained in (1), to yield a recombinant bacmid comprising the genome of the BEV for producing rAAV.

The rAAV ITR-GOI carrying the heterologous functional gene fragment is integrated through the transposon Tn7 on the shuttle plasmid with a specific site on the recombinant bacmid.

The ITR-GOI is integrated with the baculovirus genome via the shuttle plasmid, preferably, on the polyhedrin (polh) gene site. However, the shuttle plasmids can only carry exogenous DNA fragments of limited size due to their smaller genome. Conventionally, for the purpose of preparing rAAV, only one BEV is used to infect insect cell line. Therefore, the AAV Rep gene, Cap gene and ITR-GOI are all inserted into the shuttle plasmid. This increases the difficulty in constructing the shuttle plasmid and reduces the stability of the recombinant bacmid carrying a large amount of exogenous DNA fragments at a single site.

The ITR-GOI, Rep gene, and Cap gene are respectively loaded at different sites of the recombinant bacmid, so that the stability of the recombinant bacmid and the BEV prepared therefore is improved. Particularly, when the Rep gene and Cap gene are inserted in the Chia and/or Cath locus, the stability is improved greatly.

(3) The recombinant bacmid comprising the baculovirus genome for producing the rAAV obtained in (2) is used to transfect a host cell line.

Introducing the recombinant bacmid obtained in (2) into the corresponding host cell line to prepare rAAV includes but is not limited to the following manner:

Extraction and transfection: the recombinant bacmid DNA is extracted from E. coli, purified, and then used to transfect a host cell line;

Direct infection: the recombinant bacmid is used to transfect a host cell line to yield BEV; and then the BEV is used to infect the host cell line.

Extraction and transfection have relatively high virus assembly rate, and is suitable for preparing early BEV virus seed bank; direct infection has high infection efficiency, and is suitable for large-scale amplification of BEV stock for large-scale preparation of rAAV.

The disclosure provides a system for preparing rAAV, which comprises a shuttle plasmid and a corresponding recombinant bacmid comprising the baculovirus genome.

The shuttle plasmid comprises at least a rAAV ITR-GOI integrated with a heterologous functional gene fragment. The shuttle plasmid is preferably based on a pFBD plasmid. As a preferred embodiment of the disclosure, the shuttle plasmid comprises an expression cassette of a Rep gene or a Cap gene of AAV.

The recombinant bacmid comprising the baculovirus genome comprises an expression cassette of functional protein components necessary for producing rAAV. The recombinant bacmid comprising the baculovirus genome is a baculovirus without the Chia gene and/or the Cath gene. The expression cassette is inserted into the locus of one or more non-essential genes of the recombinant bacmid, such as Chia, Cath, Ac124, p10, p26, p74, ctx, egt, 39k, orf51, gp37, iap2, odv-e56.

The expression cassette of the functional protein component required for production of rAAV is inserted into the Chia and/or Cath locus of the baculovirus.

Deletion of the Chia and/or Cath gene enhances the stability of the rAAV functional proteins. The Cath and Chia loci are adjacent, which have strong load capacity.

The recombinant bacmid comprises at least one expression cassette for producing a functional protein component required for rAAV. The expression cassette of the other functional protein component required for production of rAAV is inserted into the locus of one or more non-essential genes of the recombinant bacmid, such as Chia, Cath, Ac124, p10, p26, p74, ctx, egt, 39k, orf51, gp37, iap2, odv-e56.

The expression cassette of the functional protein component required for production of rAAV is inserted into the Chia and/or Cath locus of the baculovirus.

The baculovirus genome is derived from AcMNPV, which comprises at least the expression cassette of the AAV Cap gene and/or Rep gene necessary for the assembly of rAAV The expression cassette of the functional protein component necessary for the assembly of rAAV is located downstream of and regulated by the P10 or PH promoter.

Example 1: Preparation of rAAV Using DH10Bac-Tn7-(ITR-GOI)-Cap-Δ(Chia-Cath)-Rep

Figure 2A:
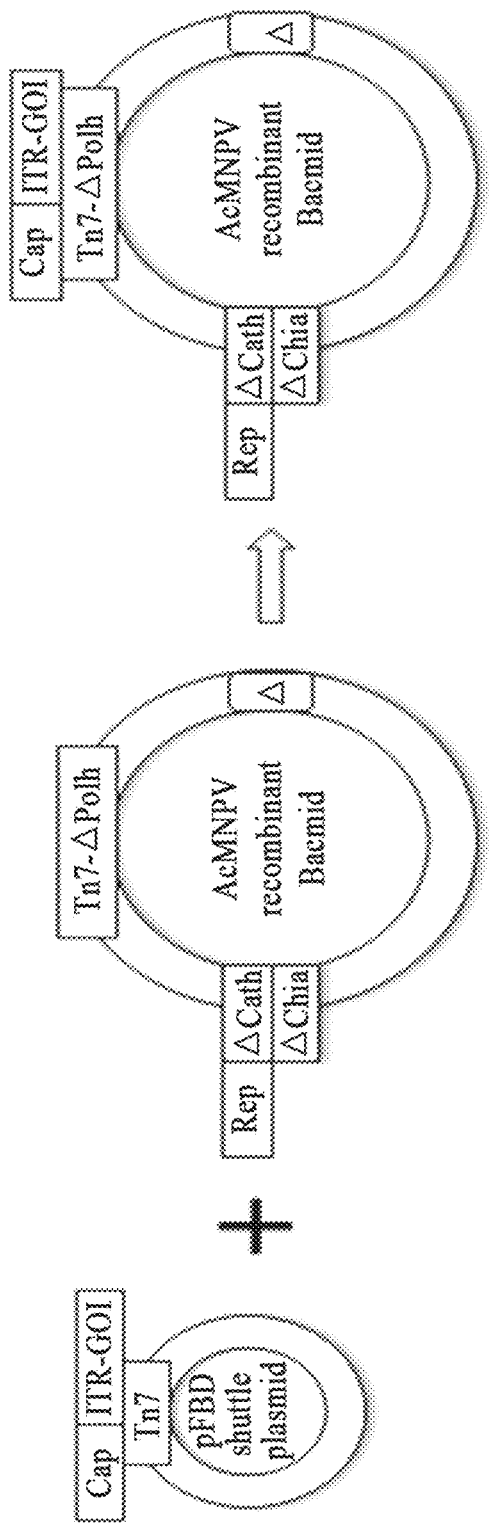
FIGS. 2A-2D show the preparation of rAAV by infecting Sf9 cells with BEV-Tn7-(ITR-GOI)-Cap-Δ(Chia-Cath)-Rep in Example 1.

The shuttle plasmid pFBD contains rAAV ITR-GOI and the expression cassette of the AAV Cap gene, and the corresponding recombinant bacmid comprises the expression cassette of the Rep gene and the expression cassette of other functional protein components of the AAV (FIG. 2A).

A system for preparing rAAV comprises a shuttle plasmid and its corresponding recombinant bacmid comprising a baculovirus genome. The shuttle plasmid is based on the plasmid pFBD. The ITR-GOI and the Cap gene are inserted at the multiple cloning site, and the Cap gene is placed downstream of the P10 promoter. The recombinant bacmid comprising a baculovirus genome is AcMNPV E2 without the non-essential genes Chia and Cath, and the gene sequence thereof is: Genbank accession No. KM667940.1. The Chia and Cath genes are deleted in the locus (position 105, 353 bp-108, 025 bp), and the expression cassette of the Rep gene is inserted into the Chia and Cath loci.

The preparation of rAAV using the rAAV preparation system comprises the following steps.

(1) Separately preparing a shuttle plasmid and a corresponding recombinant bacmid containing the baculovirus genome.

1.1 The shuttle plasmid pFBD-(ITR-GOI)-Cap containing the rAAV ITR-GOI and the expression cassette of the AVV Cap gene is constructed. The shuttle plasmid pFBD in the baculovirus expression system Bac-to-Bac is utilized. The codons based on the type 2 AAV Cap gene are optimized according to the principle of ribosome leak scanning (Smith et al., 2009, Mol, Ther. 17: 1888-1896), The P10 promoter regulates the Cap gene to achieve functional expression of three capsid proteins of VP1, VP2, and VP3 in a near natural ratio (1:1:10). With regard to the ITR-GOI, ITR selects the ITR nucleic acid sequence of type 2 AAV. The ITR-GOI adopts the expression cassette of green fluorescent protein (GFP), and the expression of GFP is controlled by the CMV promoter, which is convenient for detecting the activity of rAAV. The ITR-GOI is attached to the expression cassette of the Cap gene or vector backbone via the 5'-end nucleic acid fragment and the 3' nucleic acid fragment (For the corresponding sequence of Cap gene, ITR and its ligated fragments, see Chinese patent CN 106916793A).

1.2 Construction of recombinant bacmids without the non-essential genes Chia and Cath, and insert the expression cassette of the AAV Rep gene in the Chia and Cath loci.

The Chia and Cath genes are adjacent in the wild-type AcMNPV bacmid. This example selects the simultaneous deletion of the Chia and Cath genes as a preferred protocol. To facilitate the manipulation of recombinant cloning, the bacmid genome is engineered by Red recombinant technique using *E. coli* D141.0Bac strain transformed with pKD46 plasmid and containing AcMNPV bacmid. The pKD46 plasmid is temperature-sensitive and low-copy. The addition of arabinose can induce the expression of Exo, Beta and Gam (Red Recombinase) at 20-25° C. It is capable of efficiently and specifically recombining an exogenous DNA carrying a homology arm, and a bacmid genome in bacteria (Doublet et al, 2008, J Microbiol Methods, 75(2): 359-61). A chloramphenicol (Chlo) resistance gene (The fragment P1-FRT-Chlo-P2 on the PKD3 plasmid is amplified using the primers Frt-Chlo-F (SEQ ID NO: 9) and Frt-Chlo-R (SEQ ID NO: 10) carrying Frt sequences on both sides is introduced to facilitate screening of recombinants. Facilitating the subsequent removal of the resistance gene dependent on the action of the Flp recombinase. It can be used to continuously delete or insert a series of genes using the Chlo resistance gene, in the bacmid genome. The backbone is constructed using the pFBD shuttle plasmid from Invitrogen's Bac-to-Bac system. An upstream homology arm Chia-up and a Chlo resistance gene fragment P1-FRT-Chlo-P2 are introduced at the BsrGI restriction enzyme cutting site of the pFBD plasmid. A downstream homology arm, Cath-Down, is introduced at the AvrII restriction enzymes cutting site of the pFBD plasmid. The Rep gene and/or the Cap gene are inserted downstream of the PH promoter and/or the P10 promoter of the pFBD plasmid to constitute an expression cassette of the Rep gene and/or the Cap gene.

The codons based on the type 2 AAV Rep gene are optimized according to the principle of ribosome leak scanning (Smith et al., 2009, Mol. Ther, 17: 1888-1896). The PH promoter regulates the Rep gene to achieve functional expression of Rep72 and Rep52 proteins (For the corresponding sequences of Rep gene, see Chinese patent CN 106916793A).

The method for preparing recombinant bacmid for rAAV production is as follows:

Construct the plasmid pFBD-Chia-up-P1-FRT-Chlo-P2-Rep2-Cath-Down:

First, the wild-type AcMNPV bacmid DNA is used as a template, and the upstream homologous arm Chia-up fragment is amplified with the primers Chia-up-F (SEQ ID NO: 1) and Chia-up-R (SEQ ID NO: 2). The downstream homologous arm Cath-down fragment is amplified with the primers Cath-down-F (SEQ ID NO: 3) and Cath-down-R (SEQ in NO: 4).

The upstream homologous arm Chia-up fragment and the DNA fragment P1-FRT-Chlo-P2 containing Chlo resistance gene are cloned into psimple-T plasmid by homologous recombination to construct psimple-T1-Chia-up-P1-FRT-Chlo-P2 plasmid.

Then, the downstream homologous arm Cath-Down fragment is inserted into the AvrII restriction enzyme cutting site of the pFBD plasmid by homologous recombination method to construct a pFBD-Cath-Down plasmid. The fragment Chia-up-P1-FRT-Chlo-P2 is inserted into the BsrG restriction enzyme cutting site of the pFBD-Cath-Down plasmid by homologous recombination to construct pFBD-Chia-up-P1-FRT-Chlo-P2-Cath-Down plasmid. The Rep gene is inserted between the BamH1 and Xba1 restriction enzyme cutting sites of the pFBD-Chia-up-P1-FRT-Chlo-P2-Cath-Down plasmid, such that the Rep gene is regulated by the PH promoter. As a result, a plasmid pFBD-Chia-up-P1-FRT-Chlo-P2-Rep2-Cath-Down is obtained.

The pFBD-Chia-up-P1-FRT-Chlo-P2-Rep2-Cath-Down plasmid is double digested with BsrGI and AvrII, and the Chia-up-P1-FRT-Chlo-P2-Rep2-Cath-Down fragment is recovered by electrophoresis. Then, the DNA fragment is electro transformed into DH10Bac/pKD46 competent cells, and placed on LB plates contained three types of antibiotics, including kanamycin, tetracycline and chloramphenicol. After 48 hours of electroporation, the positive bacterial colony is picked out, and the bacmid DNA is extracted for PCR identification, and positive clones are screened for sequencing verification. The positive strain is named DH10Bac-Δ(Chia-Cath)-Rep2.

(2) The shuttle plasmid obtained in (I) and its corresponding recombinant bacmid comprising the baculovirus genome are used. The rAAV ITR-GOI carrying the heterologous functional gene fragment is integrated with the expression cassettes of the functional protein components necessary for assembly of the rAAV by using the shuttle plasmid and the recombinant bacmid obtained in (1). Thus, a recombinant bacmid comprising a BEV genome is obtained, which is capable of producing the rAAV.

BEV preparation method according to Bac-to-Bac system: the recombinant shuttle plasmid pFBD-(ITR-GOI)-Cap2 is transformed into *E. coli* DH10Bac-Δ(Chia-Cath)-Rep2 containing the corresponding recombinant bacmid using Tn7 transposon-mediated homologous recombination. As a result, *E. coli* DH10Bac-Tn7-(ITR-GOI)-Cap2-Δ(Chia-Cath)-Rep2 containing recombinant bacmids incorporating all rAAV packaging elements is obtained.

(3) The recombinant bacmid comprising the BEV genome producing the rAAV obtained in (2) is used to transfect a host cell line and cultured.

Figure 2B:
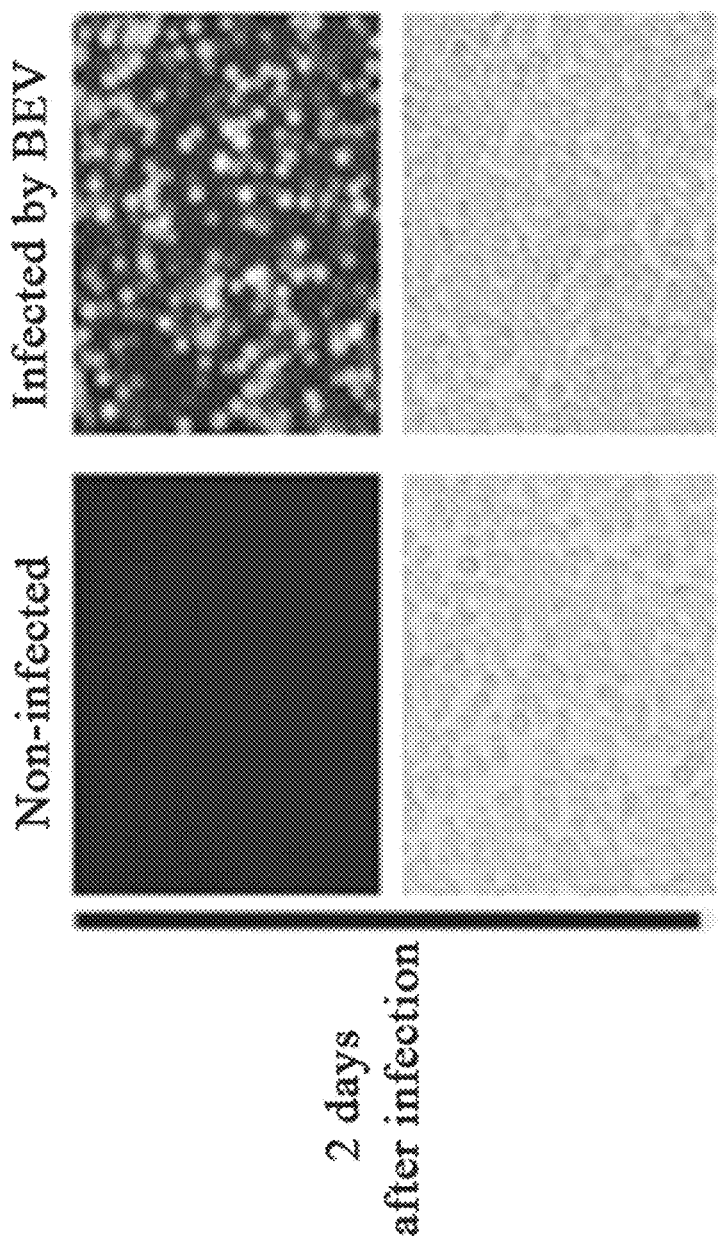

After the recombinant bacmid DNA is extracted, it is used to transfect Sf9 insect cells to prepare BEV and rAAV. The transfected Sf9 insect cells successfully produced BEV, and the Sf9 cells showed significant cytopathic effect (CPE). Significant expression of green fluorescent protein (GFP) is observed under fluorescence microscopy (FIG. 2B). The supernatant of the SP) cell culture in which CPE occurred is collected, which contained a large amount of BEV, that is, the first generation BEV (P1). At the same time, Sf9 cells containing a large amount of rAAV are collected. The suspension-cultured SP) cells is infected with prepared BEV (P1) at a multiplicity of infection (MOI=3). After 72 hours of infection, the cell culture medium is centrifuged at 3000 rpm for 5 min, and the culture supernatant and the cell pellet are separately collected. The obtained cell culture supernatant is the second-generation BEV (P2).

Purification and virus characterization of rAAV produced by this system.

Figure 7:
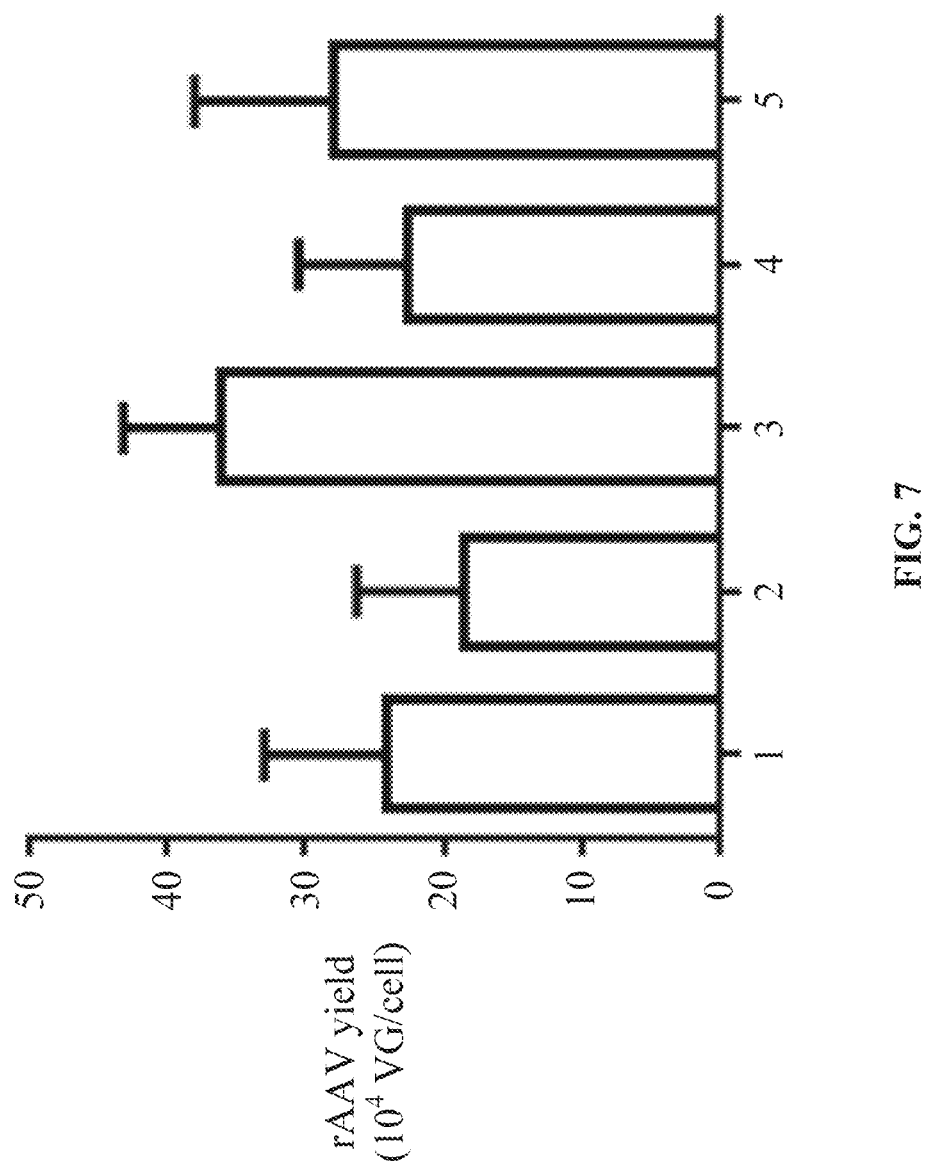
FIG. 7 illustrates the yield of the prepared rAAV in Examples 1, 2, 3, 4, 5 after Sf9 cells are infected with BEV; the yields of rAAVs were determined as VG/cell; All experiments were done in triplicate. The error bar is used to indicate the standard deviation.

The BEV infected Sf9 cells (about $1\times10^8$ cells) are added with 10 ml of lysis buffer (50 mM Tris-Cl, 150 mM NaCl, 2M $MgCl_2$, pH 8.0), and repeatedly lysed by freezing and thawing three times. The supernatant is collected by centrifugation at 5000 rpm for 10 mM, nuclease (Benzonase) is added to the supernatant, and then treated in a water bath at 37° C. for 60 min, and centrifuged at 5000 rpm for 10 min after the treatment. The collected supernatant is purified by iodixanol density gradient centrifugation (Aslanidi et al, 2009, Proc. Natl Acad. Sci. USA, 206: 5059-5064). The titer of rAAV is determined by quantitative PCR, and the titer unit is expressed by VG/mL (VG, virus genomes). The experimental results showed that the Sf9 cells infected with BEV in this example had a rAAV yield of $2.40\times10^5$ VG per cell (FIG. 7).

Figure 2C:
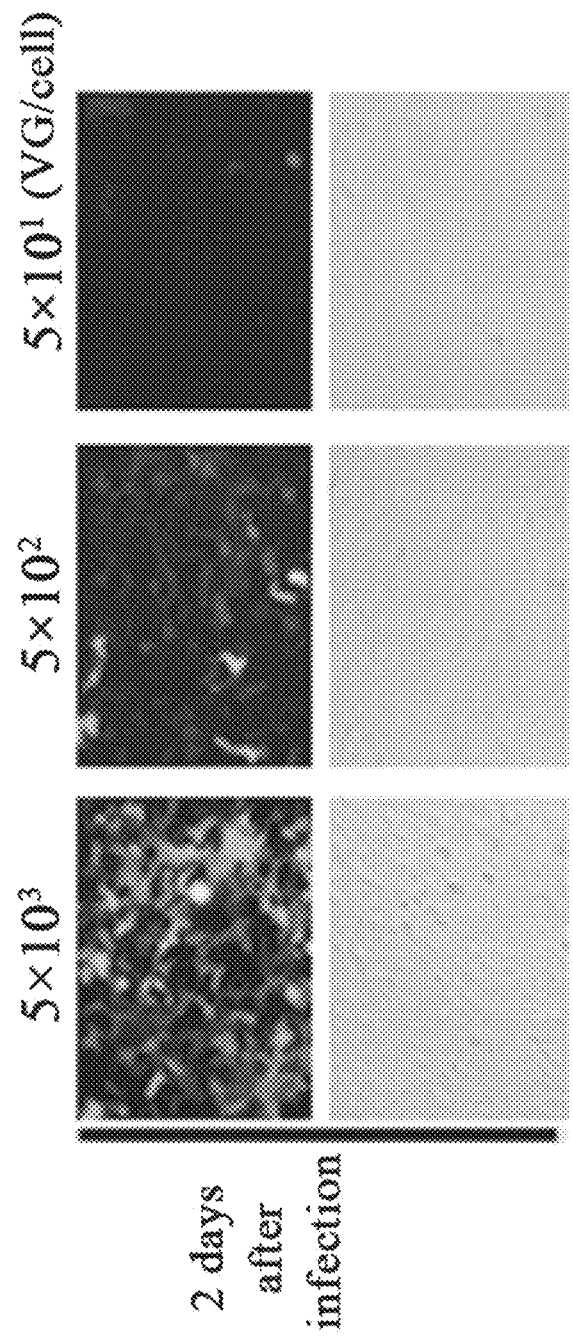

Purified rAAV is serially diluted to infect HEK293 cells cultured in 96-well plates. The expression of GFP is observed after 2 days post infection. The experimental results showed that the in vitro infection activity of rAAV prepared by the system is high (FIG. 2C).

Figure 2D:
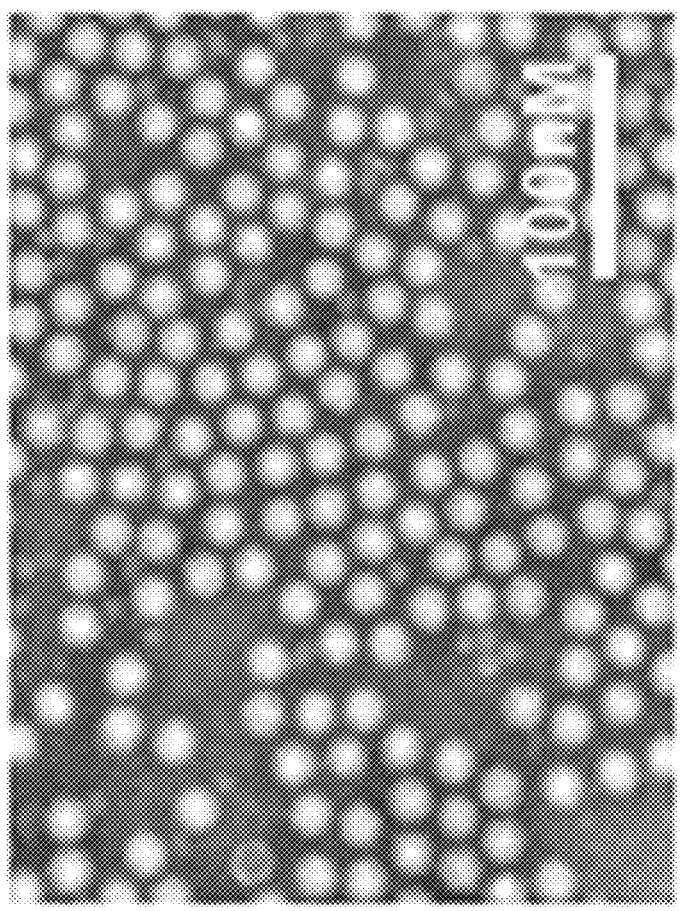

The morphology of the purified rAAV particles is observed using a transmission electron microscope. The solid intact rAAV particles are hexagonal uniform particles. The middle of hollow defective rAAV particles that do not carry nucleic acids is dyed dark. The statistical results of the electron micrographs show that the rAAV particles have a high integrity rate (FIG. 2D).

Figure 8A:
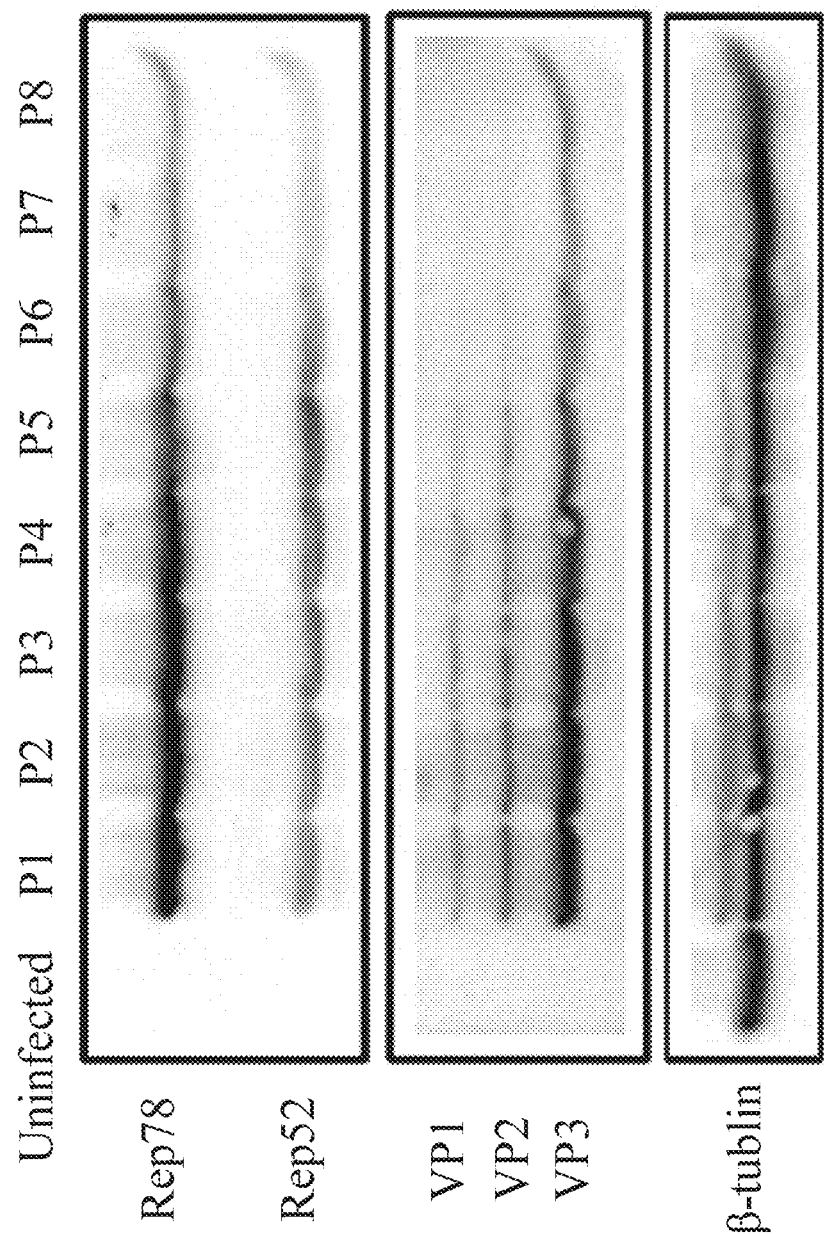
FIGS. 8A-8F are diagrams of Western blotting analysis showing the stability of BEV in Examples 1, 2, 3, 4, and 5, respectively. The Sf9 cells were infected with BEVs (from passage1 (P1) to passage8 (P8)) at a multiplicity of infection (MOI) of 3, and the expression levels of Rep and Cap proteins of AAV are detected in infected Sf9 cells, using Western blotting.
Figure 8B:
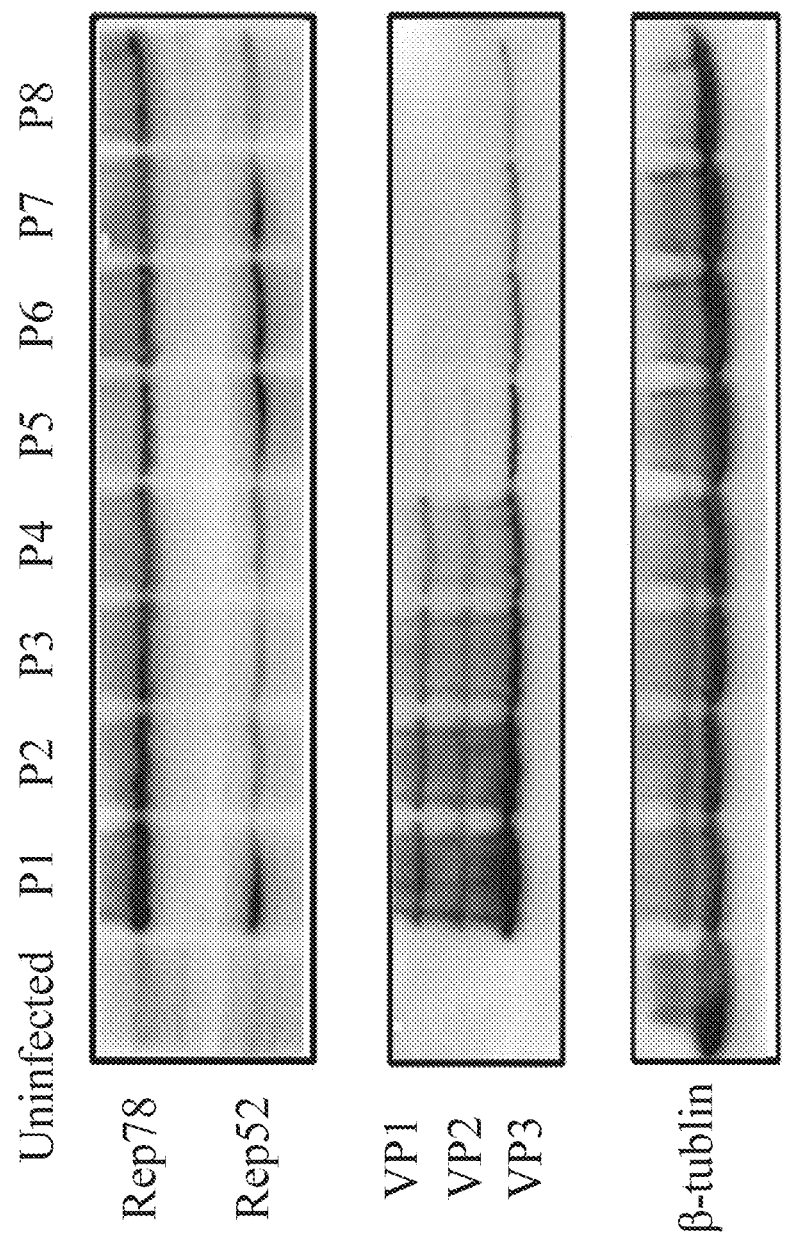

The BEV-Tn7-(ITR-GOI)-Cap2-Δ(Chia-Cath)-Rep2 prepared in this example is subject to serial passage to infect Sf9 cells. The expression of Rep and Cap proteins is detected by Western blotting and the stability of BEV is tested. Compared with the OneBac system based on shuttle plasmid, the expression levels of Rep and Cap proteins in P1-P5 generation are higher, but gradually decreased after P5 generation, and the stability of BEV also decreased significantly after P5 generation (FIG. 8A). The BEV prepared in this example is stable at P1-P4 on expression level of Cap protein, but decreased significantly from P5 to P8, while the expression level of Rep protein remained stable in P1-P8 (FIG. 8B). In summary, the stability of the BEV constructed in this example is improved to some extent.

Example 2: Preparation of rAAV Using DH10Bac-Tn7-(ITR-GOI)-Rep-Δ(Chia-Cath)-Cap

Figure 3A:
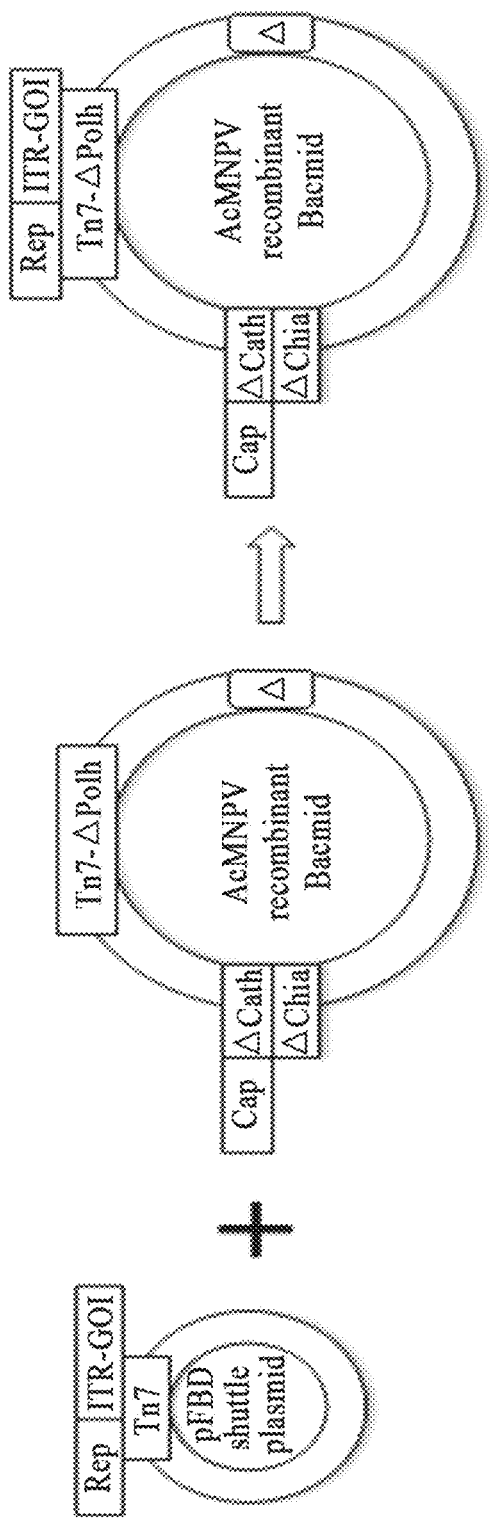
FIGS. 3A-3D show the preparation of rAAV by infecting Sf9 cells with BEV-Tn7-(ITR-GOI)-Rep-Δ(Chia-Cath)-Cap in Example 2.

The shuttle plasmid pFBD contains rAAV ITR-GOI and the expression cassette of the AAV Rep gene, and the corresponding recombinant bacmid comprises the expression cassette of the Cap gene and the expression cassette of other functional protein components of AAV (FIG. 3A).

A system for preparing rAAV comprises: a shuttle plasmid and its corresponding recombinant bacmid comprising a baculovirus genome. The shuttle plasmid is based on the plasmid pFBD, the ITR-GOI and the Rep gene are inserted at the multiple cloning site, and the Rep gene is located downstream of the PH promoter. The recombinant bacmid comprising a baculovirus genome is AcMNPV E2 without the non-essential genes Chia and Cath, and its gene sequence is, for example, Genbank accession No. KM667940.1. Within this fragment (site range 105. 353 bp-108, 025 bp), the Chia and Cath genes are deleted, and the expression cassette of the Cap gene is inserted into the Chia and Cath loci.

The preparation of rAAV using the rAAV preparation system comprises the following steps.

(1) Separately preparing a shuttle plasmid and a recombinant bacmid containing the corresponding baculovirus genome.

1.1 The shuttle plasmid pFBD-(ITR-GOI)-Rep containing the rAAV ITR-GOI and the expression cassette of the AAV Rep gene is constructed. The shuttle plasmid pFBD in the baculovirus expression system Bac-to-Bac is utilized. The codons based on the type 2 AAV Rep gene are optimized according to the principle of ribosome leak scanning (Smith et al., 2009, Mol. Ther. 17: 1888-1896). The PH promoter regulates the Rep gene to achieve functional expression of Rep72 and Rep52 proteins. With regard to the ITR-GOI, ITR selects the ITR nucleic acid sequence of type 2 AAV. The ITR-GOI adopts the expression cassette of GFP, and the expression of GFP is controlled by the CMV promoter, which is convenient for detecting the activity of rAAV. The ITR-GOI is attached to the expression cassette of Rep gene or vector backbone via the 5'-endnucleic acid fragment and the 3' nucleic acid fragment (For the corresponding sequences of Rep gene, ITR and its ligated fragments, see Chinese patent CN 106916793A).

Construction of recombinant bacmids without the non-essential genes Chia and Cath, and insert the expression cassette of the AAV Cap gene in the Chia and Cath loci.

The Chia and Cath genes are adjacent in the wild-type AcMNPV bacmid. This example selects the simultaneous deletion of the Chia and Cath genes as a preferred protocol (For the specific operation of deleting the Chia and Cath loci, refer to Example 1). For the Cap gene sequence based on type 2 AAV in this example, refer to Example 1.

The method for preparing recombinant bacmid for rAAV production is as follows:

First construct the plasmid pFBD-Chia-up-P1-FRT-Chlo-P2-Cap2-Cath-Down, the steps are as follows:

The pFBD-Chia-up-P1-FRT-Chlo-P2-Cath-Down plasmid is constructed (refer to the method of Example 1). The Cap gene is inserted between the Sma1 and Nhe1 restriction enzyme cutting sites of the plasmidpFBD-Chia-up-P1-FRT-Chlo-P2-Cath-Down, such that the Cap gene is regulated by the P10 promoter. As a result, a plasmid pFBD-Chia-up-P1-FRT-Chlo-P2-Cap2-Cath-Down is obtained.

The pFBD-Chia-up-P1-FRT-Chlo-P2-Cap2-Cath-Down plasmid is double digested with BsrGI and AvrII, and the Chia-up-P1-FRT-Chlo-P2-Cap2-Cath-Down fragment is recovered by electrophoresis. Then, the DNA fragment is electro transformed into DH10Bac/pKD46 competent cells, and placed on LB plates contained three types of antibiotics, including kanamycin, tetracycline and chloramphenicol. After 48 hours of electroporation, the positive bacterial colony is picked out, and the bacmid DNA is extracted for PCR identification, and positive clones are screened for sequencing verification. The positive strain is named DH10Bac-Δ(Chia-Cath)-Cap2.

(2) The shuttle plasmid obtained in (1) and its corresponding recombinant bacmid comprising the baculovirus genome are used. The rAAV ITR-GOI carrying the heterologous functional gene fragment is integrated with the expression cassettes of the functional protein components necessary for assembly of the rAAV by using the shuttle plasmid and the recombinant bacmid obtained in (1). Thus, a recombinant bacmid comprising a BEV genome is obtained, which is capable of producing the rAAV.

BEV preparation method according to Bac-to-Bac system: the recombinant shuttle plasmid pFBD-(ITR-GOI)-Rep2 is transformed into E. coli DH10Bac-Δ(Chia-Cath)-

Cap2 containing the corresponding recombinant bacmid using Tn7 transposon-mediated homologous recombination. Thus, E. coli DH10Bac-Tn7-(ITR-GOI)-Rep-Δ(Chia-Cath)-Cap2 containing recombinant bacmids inserting all rAAV packaging elements is obtained.

(3) The recombinant bacmid comprising the BEV genome producing the rAAV obtained in (2) is used to transfect a host cell line and cultured.

Figure 3B:
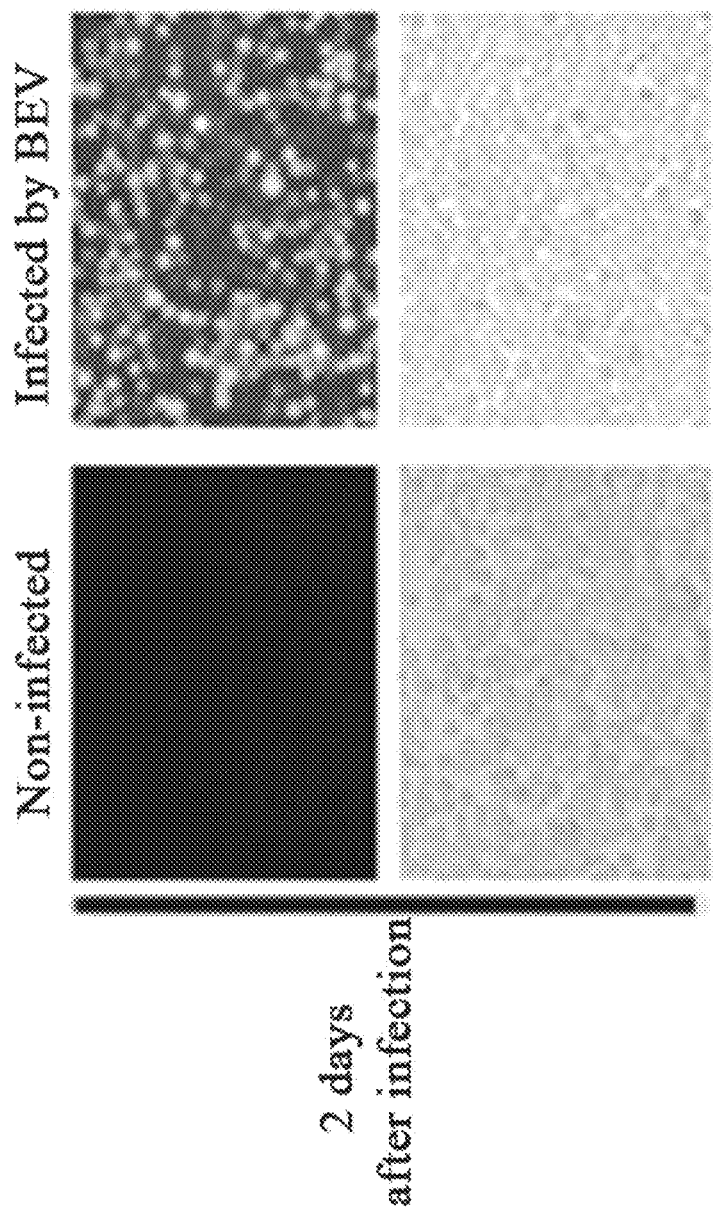

After the recombinant bacmid DNA is extracted, it is used to transfect Sf9 insect cells to prepare BEV and rAAV The transfected Sf9 insect cells successfully produced BEV, and the Sf9 cells showed significant CPE. Significant expression of green fluorescent protein (GFP) is observed under fluorescence microscopy (FIG. 3B). The supernatant of the Sf9 cell culture in which CPE occurred is collected, which contained a large amount of BEV, that is, the first-generation BEV (P1). At the same time, Sf9 cells containing a large amount of rAAV are collected. For the method of preparing BEV (P2) by passage, refer to example 1.

Purification and virus characterization of rAAV produced by this system.

The rAAV prepared by BEV-infected Sf9 cells is purified (refer to the method step in Example 1). The experimental results showed that the Sf9 cells infected with BEV in this example had a rAAV yield of $1.85 \times 10^5$ VG per cell (FIG. 7).

Figure 3C:
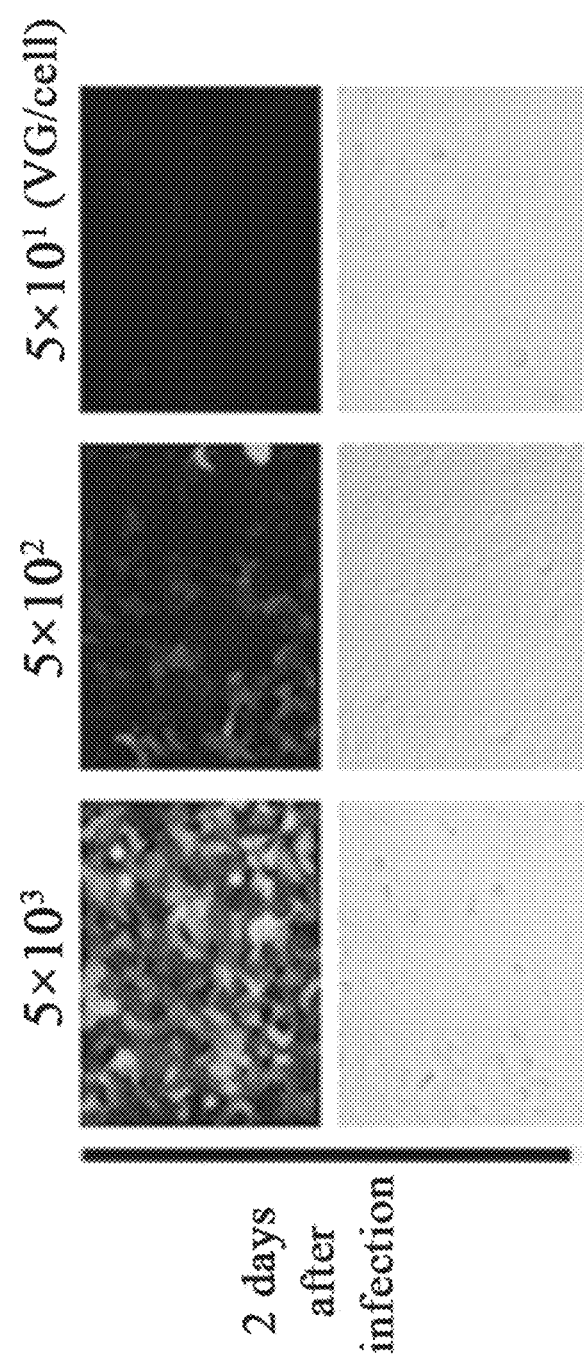

Purified rAAV is serially diluted to infect HEK293 cells cultured in 96-well plates. The expression of GFP is observed after 2 days post infection. The experimental results showed that the in vitro infection activity of rAAV prepared by the system is high (FIG. 3C).

Figure 3D:
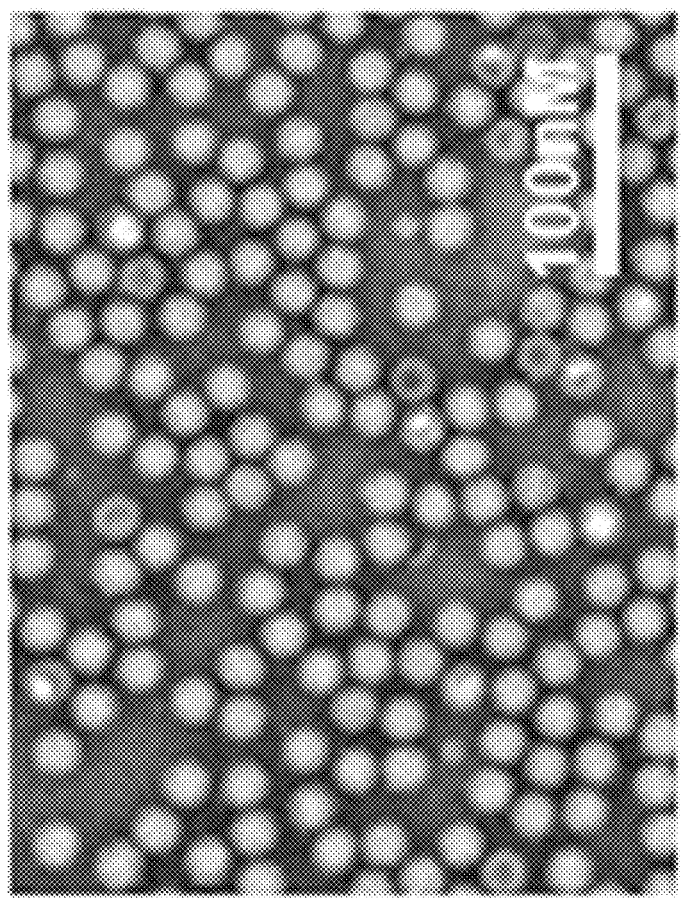

The morphology of the purified rAAV particles is observed using a transmission electron microscope. The solid intact rAAV particles are hexagonal uniform particles. The middle of hollow defective rAAV particles that do not carry nucleic acids is dyed dark. The statistical results of the electron micrographs show that the rAAV particles have a high integrity rate (FIG. 3D).

Figure 8C:
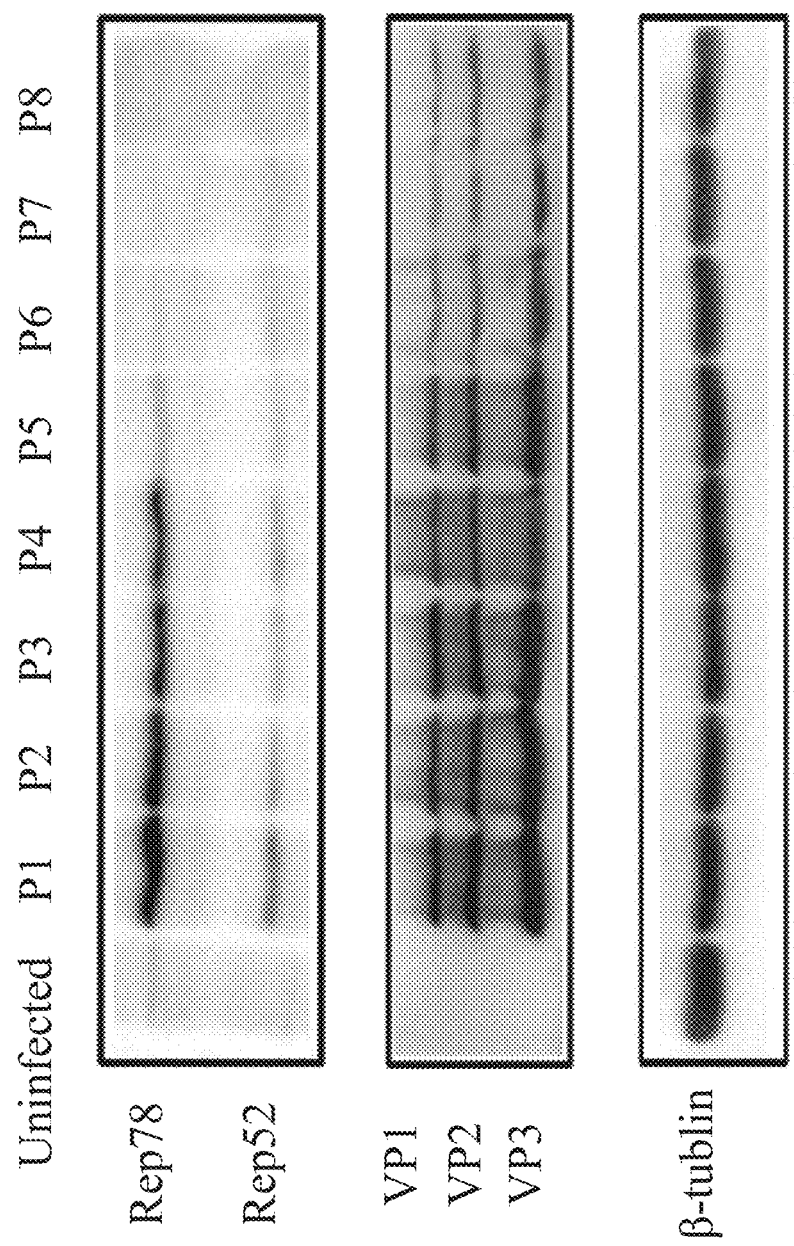

The BEV-Tn7-(ITR-GOI)-Rep2-Δ(Chia-Cath)-Cap2 prepared in this example is subject to serial passage to infect Sf9 cells. The expression of Rep and Cap proteins is detected by Western blotting and the stability of BEV is tested. Compared with the OneBac system based on shuttle plasmid, the expression levels of Rep and Cap proteins in P1-P5 generation are higher, but gradually decreased after P5 generation, and the stability of BEV also decreased significantly after P5 generation (FIG. 8A). The BEV prepared in this example is stable at P1-P4 in Rep protein expression level, but decreased significantly from P5 to P8, while the expression level of Cap protein is not significantly reduced in P1-P8 (FIG. 8C). In summary, the stability of the BEV constructed in this example is improved to some extent.

Example 3: Preparation of rAAV Using DH10Bac-Tn7-(ITR-GOI)-Δ(Chia-Cath)-Rep-Cap

Figure 4A:
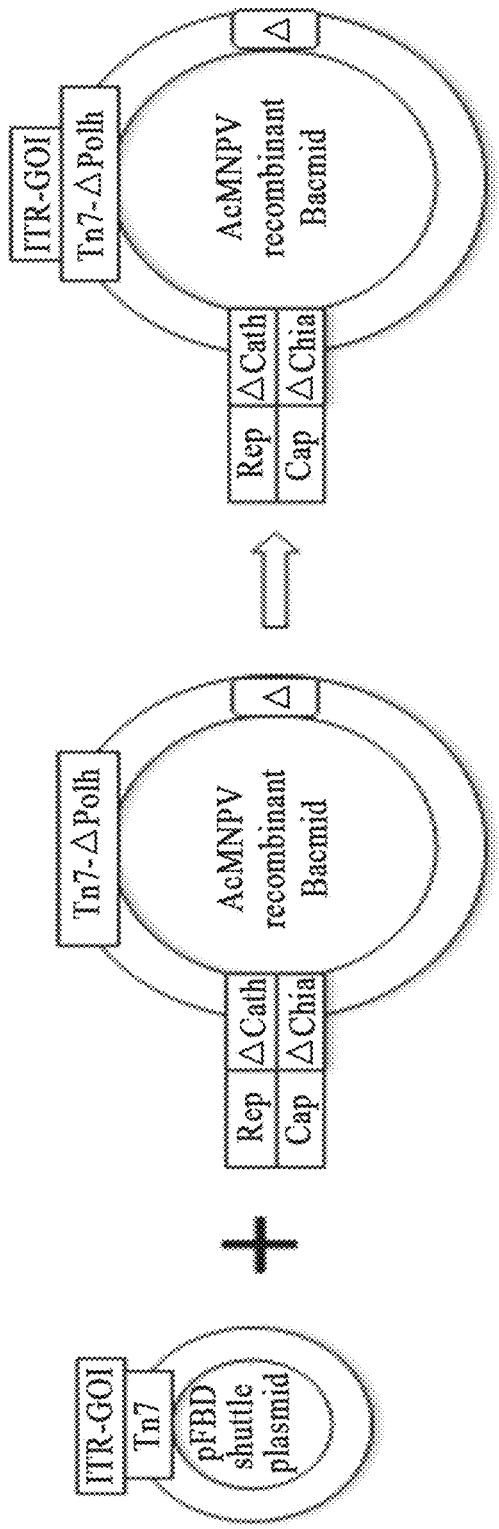
FIGS. 4A-4D show the preparation of rAAV by infecting Sf9 cells with BEV-Tn7-(ITR-GOI)-Δ(Chia-Cath)-Rep-Cap in Example 3.

The shuttle plasmid pFBD contains only the rAAV ITR-GOI, and the corresponding recombinant bacmid comprises the expression cassette of the Rep, the expression cassette of the Cap gene and the expression cassette of other functional protein components (FIG. 4A).

A system for preparing rAAV comprises: a shuttle plasmid and a corresponding recombinant bacmid comprising a baculovirus genome. The shuttle plasmid is based on the plasmid pFBD, and the ITR-GOI is inserted at the multiple cloning site. The recombinant bacmid comprising a baculovirus genome is AcMNPV E2 without the non-essential genes Cath and Chia, and its gene sequence is, for example, Genbank accession No. KM667940.1. Within this fragment (site range 105, 353 bp-108, 025 bp), the Chia and Cath genes are deleted, and the expression cassettes of the Cap and Rep gene are inserted into the Chia and Cath loci.

The preparation of rAAV using the rAAV preparation system comprises the following steps:

1) Separately preparing a shuttle plasmid and a recombinant bacmid containing the corresponding baculovirus genome.

1.1 The shuttle plasmid pFBD-(ITR-GOI) containing the rAAV ITR-GOI is constructed. Firstly, the shuttle plasmid pFBD in the baculovirus expression system Bac-to-Bac is utilized. With regard to the ITR-GOI, ITR selects the ITR nucleic acid sequence of type 2 AAV. The ITR-GOI adopts the expression cassette of GFP, and the expression of GFP is controlled by the CMV promoter, which is convenient for detecting the activity of rAAV. The ITR-GOI is attached to the vector backbone via the 5'-end nucleic acid fragment and the 3' nucleic acid fragment (For the sequences of the corresponding ITR and its ligated fragments, refer to example 1).

1.2 Construction of recombinant bacmids without the non-essential genes Chia and Cath, and insert the expression cassettes of the AAV Rep and Cap gene in the Chia and Cath loci.

The Chia and Cath genes are adjacent in the wild-type AcMNPV bacmid. This example selects the simultaneous deletion of the Chia and Cath genes as a preferred protocol (For the specific operation of deleting the Chia and Cath loci, refer to Example 1). For the Rep and Cap gene sequences based on type 2 AAV in this example, refer to Example 1.

The method for preparing recombinant bacmid for rAAV production is as follows:

First construct the plasmid pFBD-Chia-up-P1-FRT-Chlo-P2-Cap2-Cath-Down, the steps are as follows:

The pFBD-Chia-up-P1-FRT-Chlo-P2-Cath-Down plasmid is constructed (refer to the method of Example 1). The Rep gene is inserted between the BamH1 and Xba1 restriction enzyme cutting sites of the pFBD-Chia-up-P1-FRT-Chlo-P2-Cath-Down plasmid, such that the Rep gene is regulated by the PH promoter. The Cap gene is inserted between the Sma1 and Nhe1 restriction enzyme cutting sites of the pFBD-Chia-up-P1-FRT-Chlo-P2-Cath-Down plasmid, such that the Cap gene is regulated by the P10 promoter. As a result, a plasmid pFBD-Chia-up-P1-FRT-Chlo-P2-Rep2-Cap2-Cath-Down is obtained.

The pFBD-Chia-up-P1-FRT-Chlo-P2-Rep2-Cap2-Cath-Down plasmid is double digested with BsrGI and AvrII, and the Chia-up-P1-FRT-Chlo-P2-Cap2 Cath-Down fragment is recovered by electrophoresis. Then, the DNA fragment is electro transformed into DH10Bac/pKD46 competent cells, and placed on LB plates contained three types of antibiotics, including kanamycin, tetracycline and chloramphenicol. After 48 hours of electroporation, the positive bacterial colony is picked out, and the bacmid DNA is extracted for PCR identification, and positive clones are screened for sequencing verification. The positive strain is named DH10Bac-Δ(Chia-Cath)-Rep2-Cap2.

(2) The shuttle plasmid obtained in (1) and its corresponding recombinant bacmid comprising the baculovirus genome are used. The rAAV ITR-GOI carrying the heterologous functional gene fragment necessary for assembly of the rAAV is integrated with the expression cassettes of the functional protein components. Thus, a recombinant bacmid comprising a BEV genome is obtained, which is capable of producing the rAAV.

BEV preparation method according to Bac-to-Bac system: the recombinant shuttle plasmid pFBD-(ITR-GOI) is transformed into E. coli DH10Bac-Δ(Chia-Cath)-Rep2-Cap2 containing the corresponding recombinant bacmid using Tn7 transposon-mediated homologous recombination. Thus, E. coli DH10Bac-Tn7-(ITR-GOI)-Δ(Chia-Cath)-Rep2-Cap2 containing recombinant bacmids inserting all rAAV packaging elements is obtained.

Figure 4B:
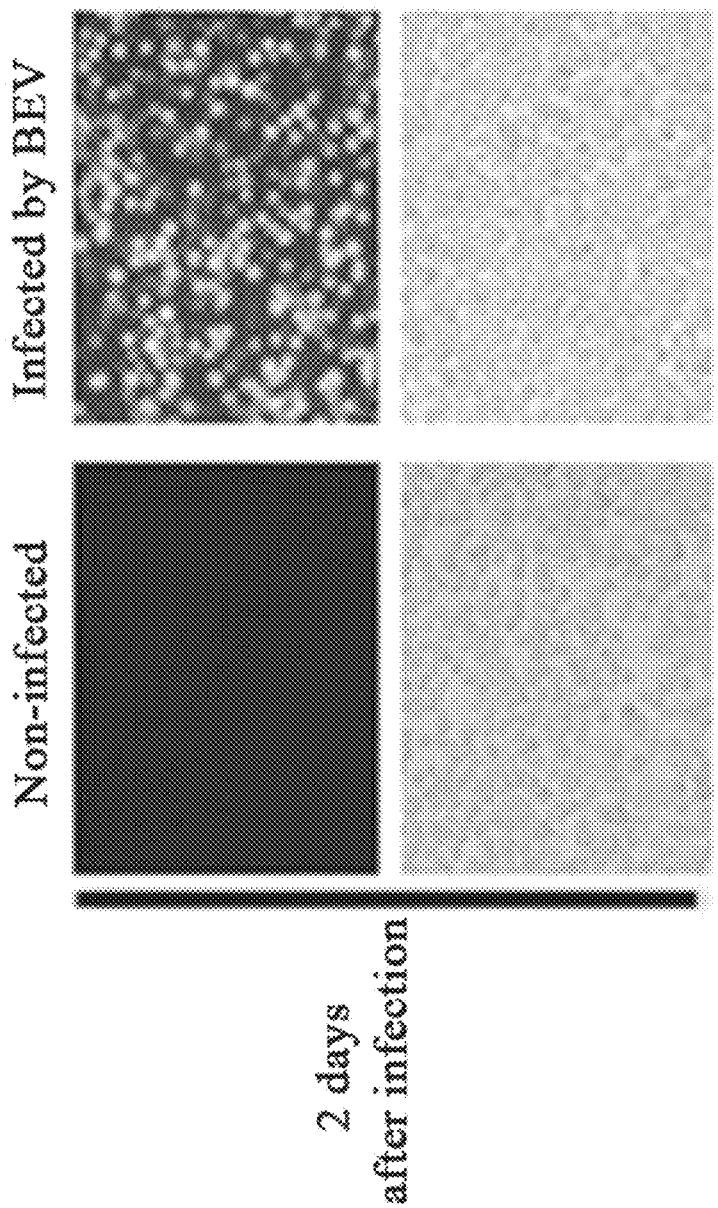

(3) The recombinant bacmid comprising the BEV genome producing the rAAV obtained in (2) is used to transfect a host cell line and cultured. After the recombinant bacmid DNA is extracted, it is used to transfect Sf9 insect cells to prepare BEV and rAAV. The transfected Sf9 insect cells successfully produced BEV, and the Sf9 cells showed significant CPE. Significant expression of green fluorescent protein (GFP) is observed under fluorescence microscopy (FIG. 4B). The supernatant of the Sf9 cell culture in which CPE occurred is collected, which contained a large amount of BEV, that is, the first-generation BEV (P1). At the same time, SN cells containing a large amount of rAAV are collected. For the method of preparing BEV (P2) by passage, refer to example 1.

Purification and virus characterization of rAAV produced by this system.

The rAAV prepared by BEV-infected Sf9 cells is purified (refer to the method step in Example 1). The experimental results showed that the Sf9 cells infected with BEV in this example had a rAAV yield of $3.60 \times 10^5$ VG per cell (FIG. 7).

Figure 4C:
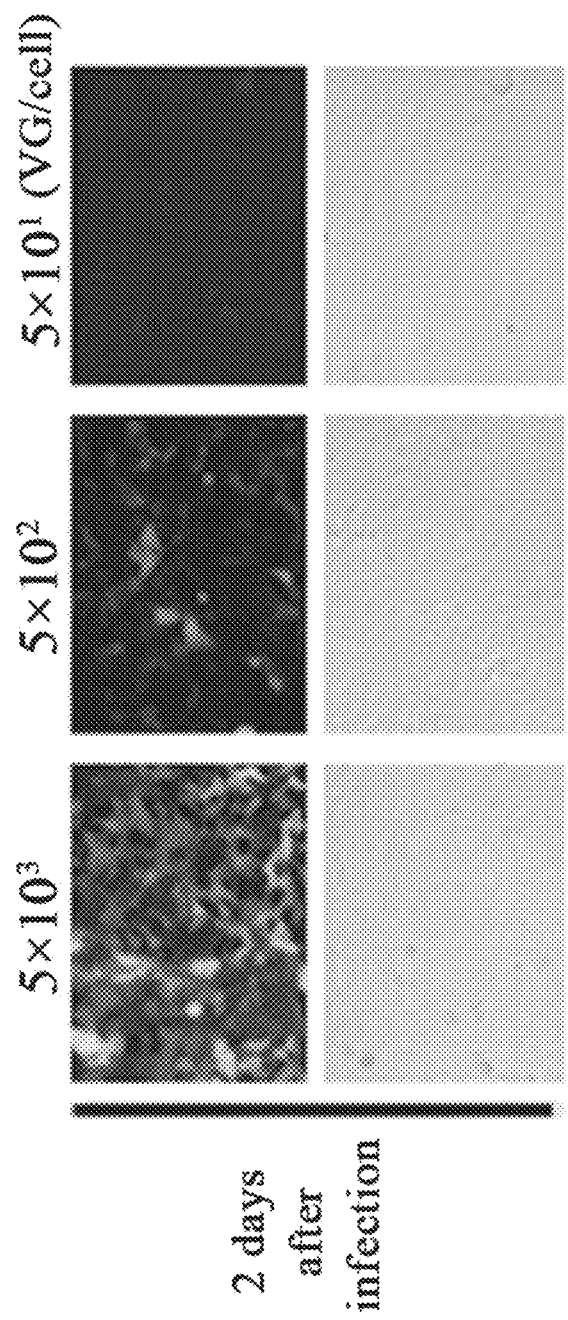

Purified rAAV is serially diluted to infect HEK293 cells cultured in 96-well plates. The expression of GFP is observed with a fluorescence microscope, after 2 days post infection. The experimental results showed that the in vitro infection activity of rAAV prepared by the system is high (FIG. 4C).

Figure 4D:
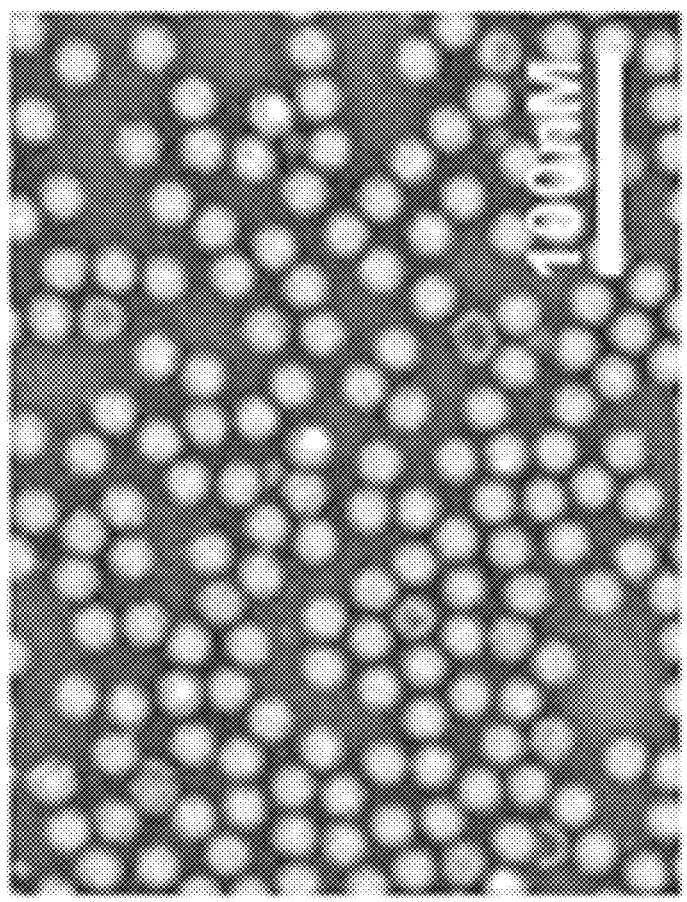

The morphology of the purified rAAV particles is observed using a transmission electron microscope. The solid intact rAAV particles are hexagonal uniform particles. The middle of hollow defective rAAV particles that do not carry nucleic acids is dyed dark. The statistical results of the electron micrographs show that the rAAV particles have a high integrity rate (FIG. 4D).

Figure 8D:
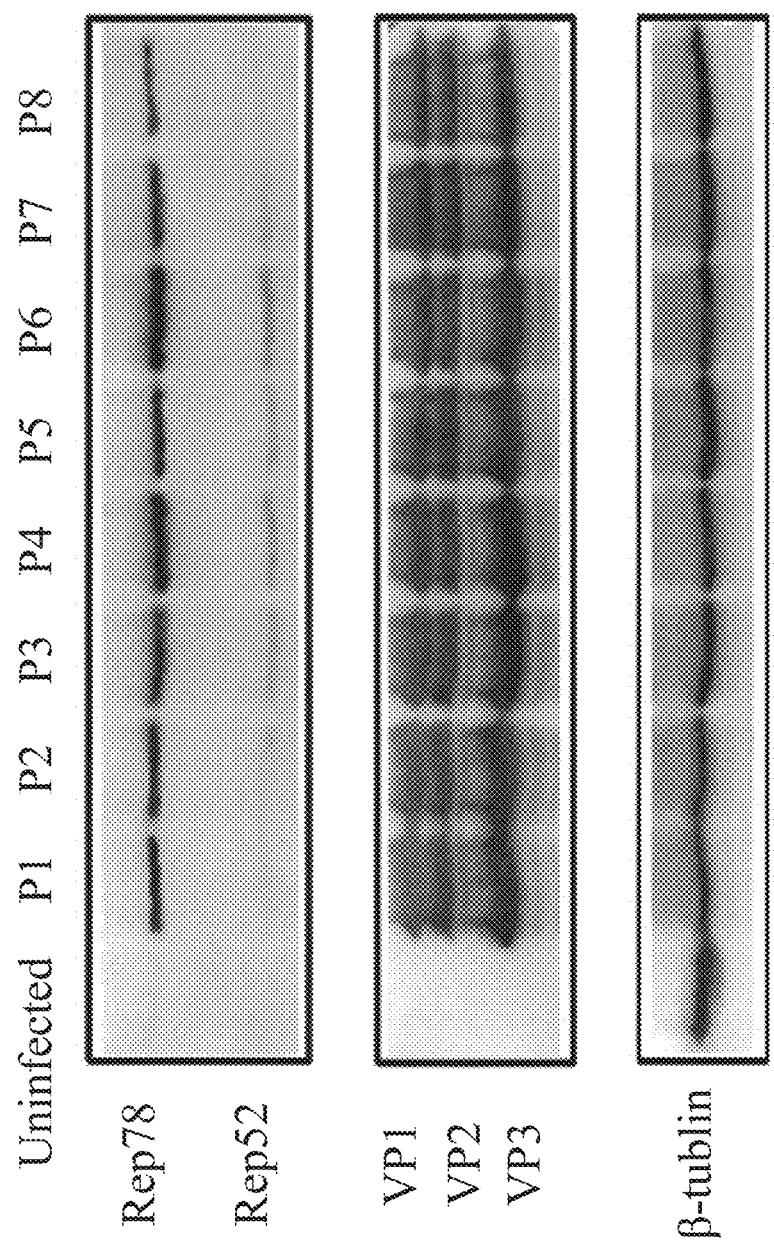

The BEV-Trig-(ITR-GOI)-Δ(Chia-Cath)-Rep2-Cap2 prepared in this example is subject to serial passage to infect SN cells. The expression of Rep and Cap proteins is detected by Western blotting and the stability of BEV is tested. Compared with the OneBac system based on shuttle plasmid, the expression levels of Rep and Cap proteins in P1-P5 generation are higher, but gradually decreased after P5 generation, and the stability of BEV also decreased significantly after P5 generation (FIG. 8A). The BEV prepared in this example is stable at P1-P8 generation in both Rep and Cap protein expression level (FIG. 8D). In summary, the stability of the BEV constructed in this example has been greatly improved.

Figure 5A:
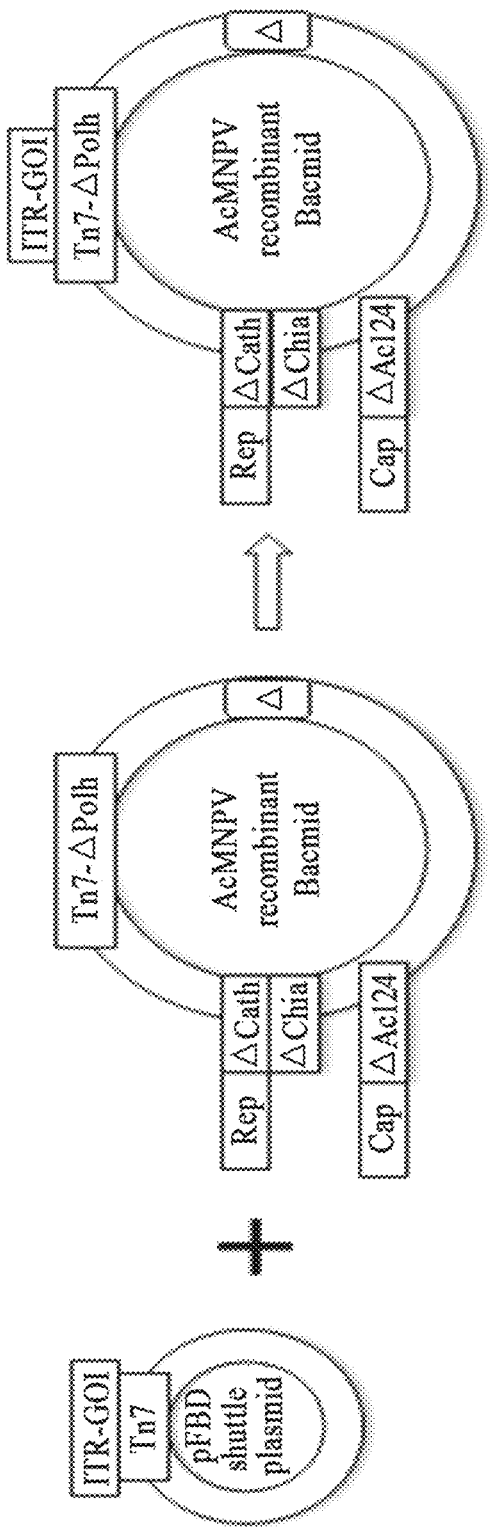
FIGS. 5A-5D show the preparation of rAAV by infecting Sf9 cells with BEV-Tn7-(ITR-GOI)-Δ(Chia-Cath)-Rep-ΔAc124-Cap in Example 4.

Example 4: Preparation of rAAV Using DH10Bac-Tn7-(ITR-GOI)-Δ(Chia-Cath)-Rep-ΔAc124-Cap A system for preparing rAAV comprises: a shuttle plasmid and a corresponding recombinant bacmid comprising a baculovirus genome. The shuttle plasmid is based on the plasmid pFBD, and the ITR-GOI is inserted at the multiple cloning site. The recombinant bacmid comprising a baculovirus genome is AcMNPV E2 without the non-essential genes Cath, Chia and Ac124, and its gene sequence is, for example, Genbank accession No. KM667940.1. Within the fragment (site range 105, 353 bp-108, 025 bp), the Chia and Cath genes are deleted, and within the fragment (site range 103,864 bp-104,607 bp), the Ac124 gene is deleted. The expression cassettes of the Rep gene are inserted into the Chia and Cath loci, and the expression cassettes of the Cap gene are inserted into the Ac124 loci (FIG. 5A).

This example is based on the strain of E. coli DH10Bac-Δ(Chia-Cath)-Rep2 containing the recombinant bacmid in Example 1, and the expression cassette of the Cap gene is inserted into other non-essential loci. The non-essential gene Ac-124 is preferred in this example (refer to Liang et al., 2015, Arch Virol, 160(1): 275-84).

The preparation of rAAV using the rAAV preparation system comprises the following steps.

1) Separately preparing a shuttle plasmid and a recombinant bacmid containing the corresponding baculovirus genome.

The shuttle plasmid pFBD-(ITR-GOI) containing the rAAV ITR-GOI is constructed. Refer to the scheme in Example 3.

1.2 Construction of recombinant bacmids without the non-essential genes Chia, Cath and Ac124, then insert the expression cassettes of the AAV Rep gene in the Chia and Cath loci and insert the expression cassettes of the AAV Cap gene at the Ac124 loci.

To perform a new round of Red recombination at the non-essential gene Ac-124 locus, it is necessary to remove the chloramphenicol (Chlo) resistance gene in the recombinant bacmid genome of E. coli DH10Bac-Δ(Chia-Cath)-Rep2 in Example 1. The pCP20 plasmid is a temperature-sensitive plasmid that induces expression of FLP recombinase (refer to Doublet et al, 2008, J Microbiol Methods, 75(2): 359-61).

The pCP20 plasmid is first transformed into DH10Bac-Δ(Chia-Cath)-Rep and plated on LB plates contained three types of antibiotics, including kanamycin, tetracycline and ampicillin. The cells are cultured at 30° C. for 48 h, colonies are picked for PCR identification using FLP primers and screening for positive bacteria. Then, the DH10Bac-Δ(Chia-Cath)-Rep2 strain transformed with the pCP20 plasmid is placed in kanamycin, tetracycline, and ampicillin-resistant liquid LB medium. The strain is cultured at 42° C. for 8 hours to induce the expression of the FLP recombination enzyme gene. The Chlo gene in the Frt element is removed. The strain without Chol resistance is picked for PCR identification. The positive strain is named: DH10Bac-Δ(Chia-Cath)-Rep2-ΔChlo.

To facilitate the manipulation of recombinant cloning, the bacmid genome is engineered using the DH10Bac-Δ (Chia-Cath)-Rep2-ΔChlo strain transformed with the pKD46 plasmid in combination by using the Red recombination technique (The principle and method thereof, refer to Example 1). An upstream homology arm Ac124-up and a Chlo resistance gene fragment P1-FRT-Chlo-P2 are inserted into the BsrGI restriction enzyme cutting site of the pFBD plasmid. The downstream homology arm Ac124-Down is inserted into the AvrII restriction enzyme cutting site of the pFBD plasmid. The Rep gene and/or the Cap gene are inserted into the downstream of the PH promoter and/or the P10 promoter of the pFBD plasmid to constitute an expression cassette of the Rep gene and/or the Cap gene. The Cap gene sequence based on type 2 AAV in this example, refer to Example 1.

The method for preparing recombinant bacmid for rAAV production is as follows:

First construct the plasmid pFBD-Ac124-up-P1-FRT-Chlo-P2-Cap2-Ac124-Down, the steps are as follows:

First, the wild-type AcMNPV bacmid DNA is used as a template, and the upstream homologous arm Ac124-up fragment is amplified with the primers Ac124-up-F (SEQ ID NO: 5) and Ac124-up-R (SEQ ID NO: 6). The downstream homologous arm Ac124-down fragment is amplified with the primers Ac124-down-F (SEQ ID NO: 7) and Ac124-down-R (SEQ In NO: 8).

Then, the upstream homologous arm Ac124-up fragment and a Chlo resistance gene fragment P1-FRT-Chlo-P2 is inserted into the psimple-T plasmid by homologous recombination method to construct a psimple-T-Ac124-up-P1-FRT-Chlo-P2 plasmid.

The downstream homology arm Ac124-Down is inserted into the AvrII restriction enzyme cutting site of the pFBD plasmid by homologous recombination method to construct a pFBD-Ac124-Down plasmid. And the fragment Ac124-up-P1-FRT-Chlo-P2 is inserted into the BsrG1 restriction enzyme cutting site of the pFBD-Ac124-Down plasmid by homologous recombination method to construct a pFBD-Ac124-up-P1-FRT-Chlo-P2-Ac124-Down plasmid.

The Cap gene is inserted between the Sma1 and Nhe1 restriction enzyme cutting sites of the pFBD-Ac124-up-P1-FRT-Chlo-P2-Ac124-Down plasmid, such that the Cap gene is regulated by the P10 promoter. As a result, a plasmid pFBD-Ac124-up-P1-FRT-Chlo-P2-Cap2-Ac124-Down is obtained.

The pFBD-Ac124-up-P1-FRT-Chlo-P2-Cap2-Ac124-Down plasmid is double digested with BsrGI and AvrII, and the Ac124-up-P1-FRT-Chlo-P2-Cap2-Ac124-Down fragment is recovered by electrophoresis. Then, the DNA fragment is electro transformed into DH10Bac-Δ(Chia-Cath)-Rep2-ΔChlo/pKD46 competent cells, and placed on LB plates contained three types of antibiotics, including kanamycin, tetracycline and chloramphenicol. After 48 h of electroporation, the positive bacterial colony s picked out, and the bacmid DNA is extracted for PCR identification, and positive clones are screened for sequencing verification. The positive strain is named DH10Bac-Δ(Chia-Cath)-Rep2-ΔAc124-Cap2.

(2) The shuttle plasmid obtained in (1) and its corresponding recombinant bacmid comprising the baculovirus genome are used. The rAAV ITR-GOI carrying the heterologous functional gene fragment is integrated with the expression cassettes of the functional protein components necessary for assembly of the rAAV by using the shuttle plasmid and the recombinant bacmid obtained in (1). Thus, a recombinant bacmid comprising a BEV genome is obtained, which is capable of producing the rAAV.

BEV preparation method according to Bac-to-Bac system: the recombinant shuttle plasmid pFBD-(ITR-GOI) is transformed into E. coli DH10Bac-Δ(Chia-Cath)-Rep2-ΔAc124-Cap2 containing the corresponding recombinant bacmid using Tn7 transposon-mediated homologous recombination. As a result, E. Coli DH10Bac-Tn7-(ITR-GOI)-Δ(Chia-Cath)-Rep2-ΔAc124-Cap2 containing recombinant bacmids incorporating all rAAV packaging elements is obtained.

(3) The recombinant bacmid comprising the BEV genome producing the rAAV obtained in (2) is used to transfect a host cell line and cultured.

Figure 5B:
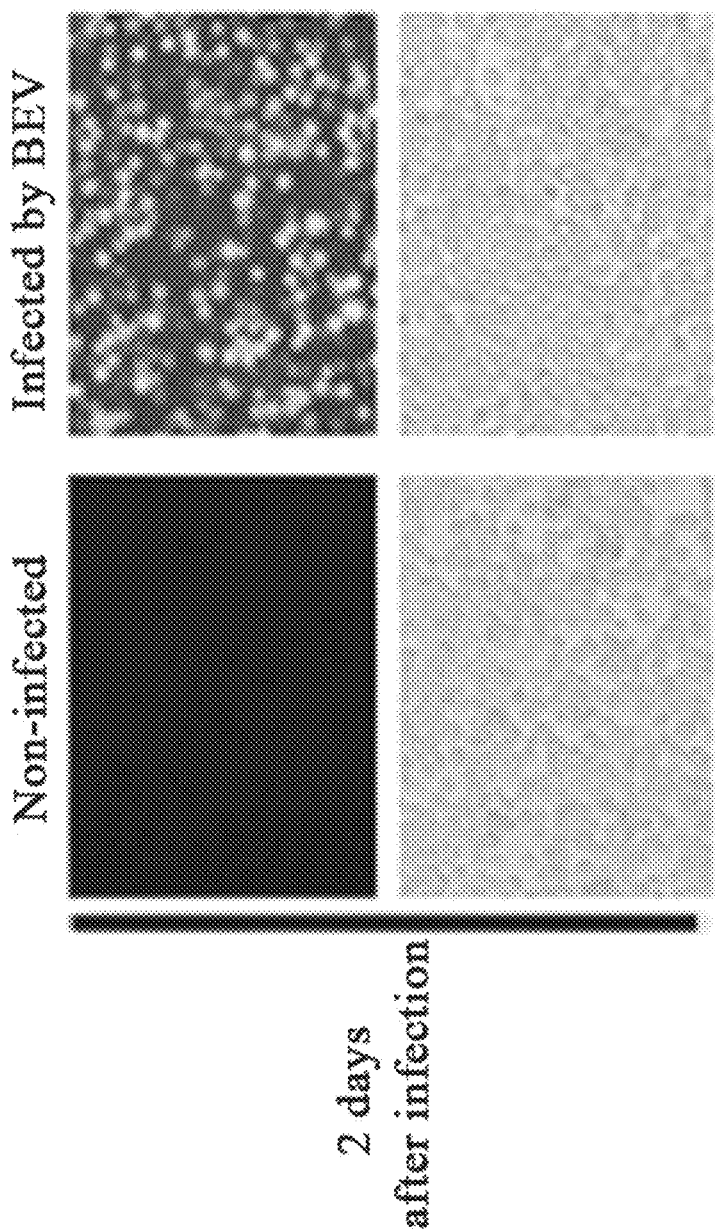

After the recombinant bacmid DNA is extracted, it is used to transfect Sf9 insect cells to prepare BEV and rAAV. The transfected SP insect cells successfully produced BEV, and the Sf9 cells showed significant CPE. Significant expression of green fluorescent protein (GFP) is observed under fluorescence microscopy (FIG. 5B). The supernatant of the SP cell culture in which CPE occurred is collected, which contained a large amount of BEV, that is, the first-generation BEV (P1). At the same time, Sf9 cells containing a large amount of rAAV are collected. For the method of preparing BEV (P2) by passage, refer to example 1.

Purification and virus characterization of rAAV produced by this system.

The rAAV prepared by BEV-infected Sf9 cells is purified (refer to the method step in Example 1). The experimental results showed that the SN cells infected with BEV in this example had a rAAV yield of $2.27 \times 10^5$ VG per cell (FIG. 7).

Figure 5C:
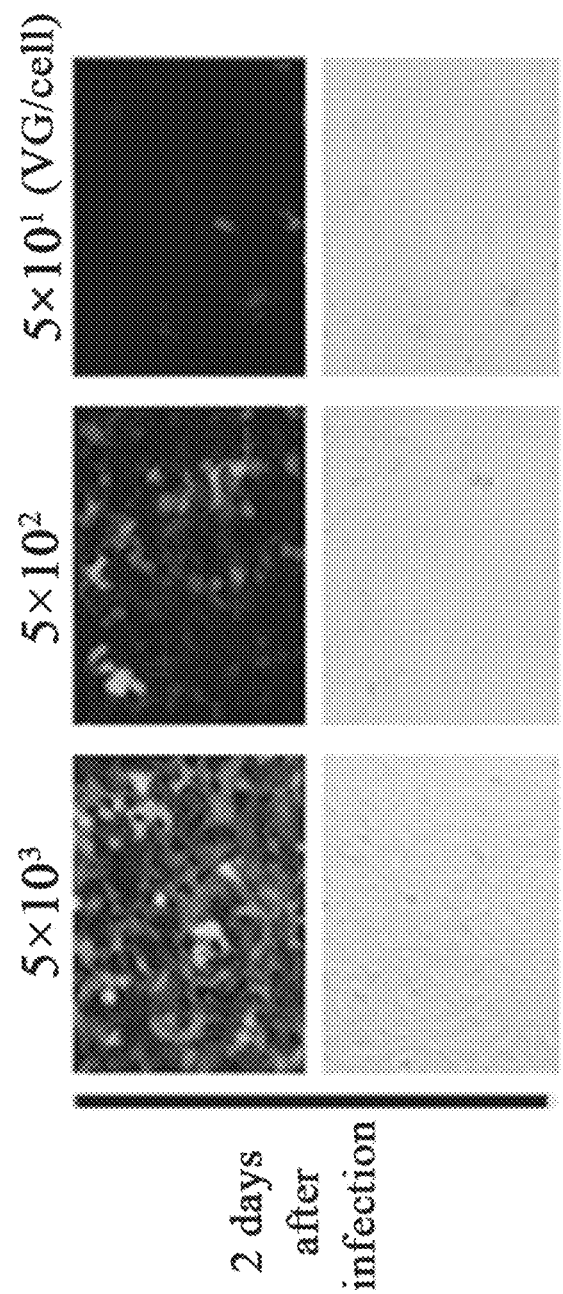

Purified rAAV is serially diluted to infect HEK293 cells cultured in 96-well plates. The expression of GFP is observed after 2 days post infection. The experimental results showed that the in vitro infection activity of rAAV prepared by the system is high (FIG. 5C).

Figure 5D:
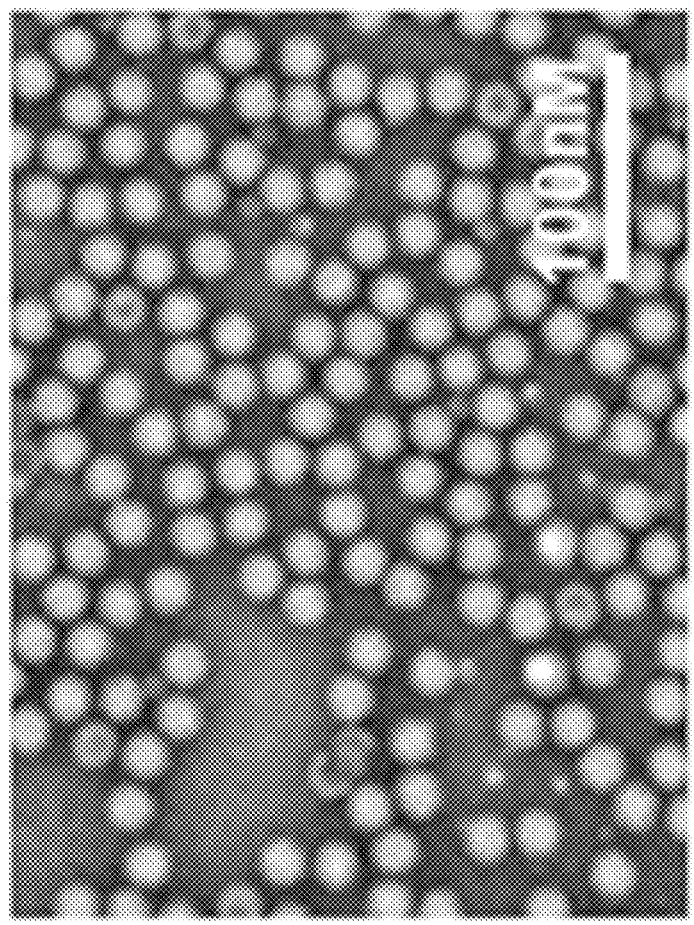

The morphology of the purified rAAV particles is observed using a transmission electron microscope. The solid intact rAAV particles are hexagonal uniform particles. The middle of hollow defective rAAV particles that do not carry nucleic acids is dyed dark. The statistical results of the electron micrographs show that the rAAV particles have a high integrity rate (FIG. 5D).

Figure 8E:
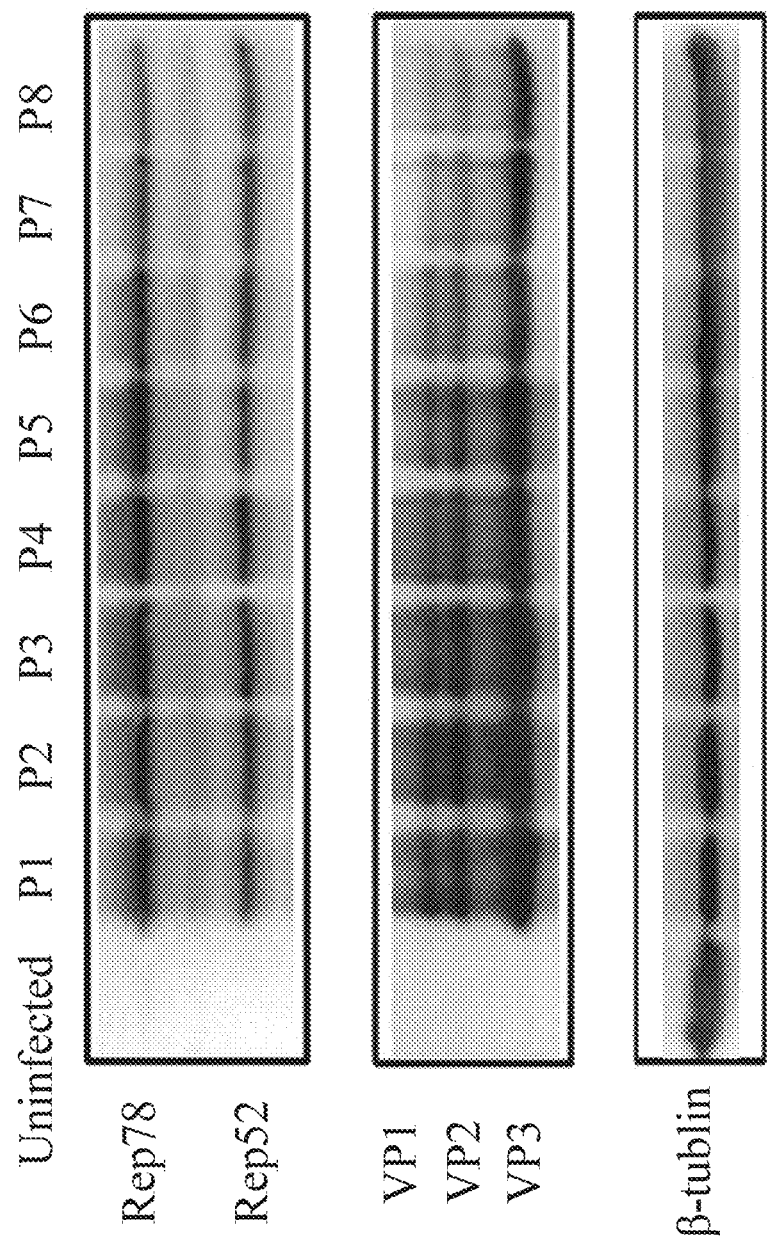

The BEV-Tn7-(ITR-GOI)-Δ(Chia-Cath)-Rep2-ΔAc124-Cap2 prepared in this example is subject to serial passage to infect Sf9 cells. The expression of Rep and Cap proteins is detected by Western blotting and the stability of BEV is tested. Compared with the OneBac system based on shuttle plasmid, the expression levels of Rep and Cap proteins in P1-P5 generation are higher, but gradually decreased after P5 generation, and the stability of BEV also decreased significantly after P5 generation (FIG. 8A). The BEV prepared in this example is stable at P1-P8 generation in both Rep and Cap proteins expression levels (FIG. 8E). In summary, the stability of the BEV constructed in this example has been greatly improved.

Figure 6A:
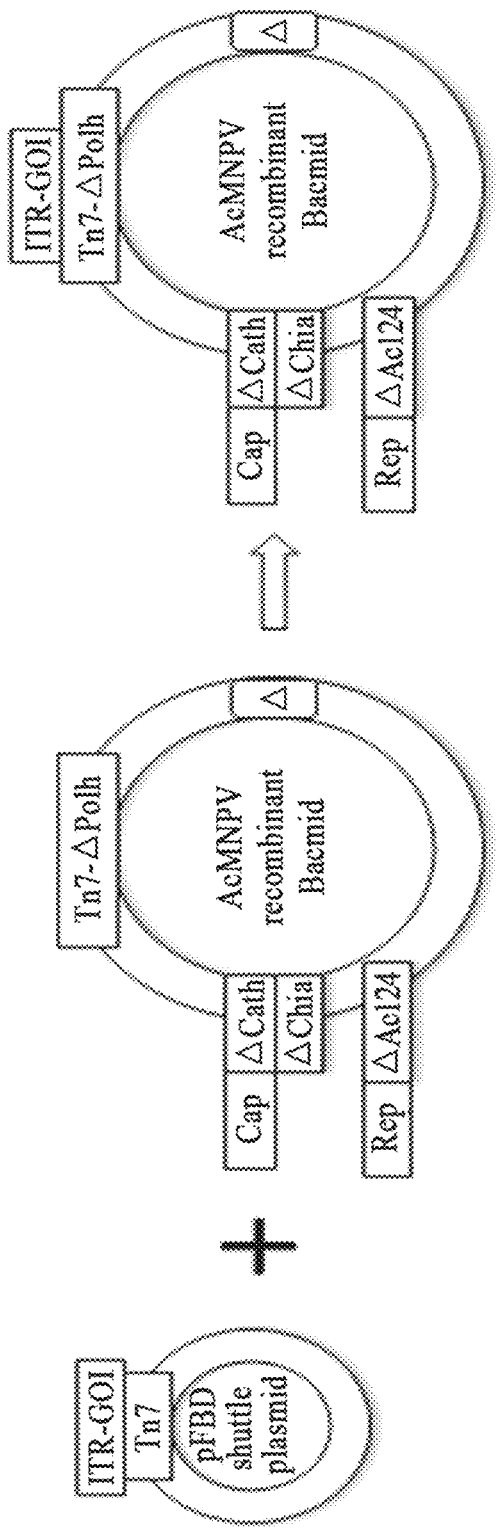
FIGS. 6A-6D show the preparation of rAAV by infecting Sf9 cells with BEV-Tn7-(ITR-GOI)-Δ(Chia-Cath)-Cap-ΔAc124-Rep in Example 5.

Example 5: Preparation of rAAV Using DH10Bac-Tn7-(ITR-GOI)-Δ(Chia-Cath)-Cap-ΔAc124-Rep A system for preparing rAAV comprises: a shuttle plasmid and a corresponding recombinant bacmid comprising a baculovirus genome. The shuttle plasmid is based on the plasmid pFBD, and the ITR-GOI is inserted at the multiple cloning site. The recombinant bacmid comprising a baculovirus genome is AcMNPV E2 without the non-essential genes Cath, Chia and Ac124, and its gene sequence is, for example, Genbank accession No. KM667940.1. Within the fragment (site range 105, 353 bp-108, 025 bp), the Chia and Cath genes are deleted, and within the fragment (site range 103,864bp-104,607bp), the Ac124 gene is deleted. The expression cassettes of the Cap gene are inserted into the Chia and Cath loci, and the expression cassettes of the Rep gene are inserted into the Ac124 loci (FIG. 6A).

This example is based on the strain of E. coli DH10Bac-Δ(Chia-Cath)-Cap2 containing the recombinant bacmid in Example 1, and the expression cassette of the Rep gene is inserted into other non-essential loci. The non-essential gene Ac-124 is preferred in this example (refer to Liang et al., 2015, Arch Virol, 160(1): 275-84).

The preparation of rAAV using the rAAV preparation system comprises the following steps.

1) Separately preparing a shuttle plasmid and a recombinant bacmid containing the corresponding baculovirus genome.

1.1 The shuttle plasmid pFBD-(ITR-GOI) containing the rAAV ITR-GOI is constructed. Refer to the scheme in Example 3.

1.2 Construction of recombinant bacmids without the non-essential genes Chia, Cath and Ac124 loci, then insert the expression cassettes of the AAV Cap gene in the Chia and Cath loci and insert the expression cassettes of the AAV Rep gene at the Ac124 loci.

To perform a new round of Red recombination at the non-essential gene Ac-124 locus, it is necessary to remove the chloramphenicol (Chlo) resistance gene on the recombinant bacmid genome of E. coli DH10Bac-Δ(Chia-Cath)-Cap2 in Example 2. Construction of strain DH10Bac-Δ(Chia-Cath)-Cap2-ΔChlo, refer to the method in Example 4.

To facilitate the manipulation of recombinant cloning, the bacmid genome is engineered using the DH10Bac-Δ(Chia-Cath)-Cap2-ΔChlo strain transformed with the pKD46 plasmid in combination with the technique of Red recombination (The principle and method thereof, refer to the Example 1). An upstream homology arm Ac124-up and a Chlo resistance gene fragment P1-FRT-Chlo-P2 are inserted into the BsrGI restriction enzyme cutting site of the pFBD plasmid. The downstream homology arm Ac124-Down is inserted into the AvrII restriction enzyme cutting site of the pFBD plasmid. The Rep gene and/or the Cap gene are inserted into the downstream of the PH promoter and/or the P10 promoter of the pFBD plasmid to constitute an expression cassette of the Rep gene and/or the Cap gene. The Rep gene sequence based on type 2 AAV in this example, refer to Example 1.

The method for preparing recombinant bacmid for rAAV production is as follows:

First construct the plasmid pFBD-Ac124-up-P1-FRT-Chlo-P2-Rep2-Ac124-Down, the steps are as follows:

The pFBD-Ac124-up-P1-FRT-Chlo-P2-Ac124-Down plasmid is constructed (refer to the method of Example 4).

The Rep gene is inserted between the BamH1 and Xha1 restriction enzyme cutting sites of the pFBD-Ac124-up-P1-FRT-Chlo-P2-Ac124-Down plasmid, such that the Rep gene is regulated by the PH promoter. As a result, a plasmid pFBD-Ac124-up-P1-FRT-Chlo-P2-Rep2-Ac124-Down is obtained.

The pFBD-Ac124-up-P1-FRT-Chlo-P2-Ac124-Down plasmid is double digested with BsrGI and AvrII, and the Ac124-up-P1-FRT-Chlo-P2-Rep2-Ac124-Down fragment is recovered by electrophoresis. Then, the DNA fragment is electro transformed into DH10Bac-Δ(Chia-Cath)-Cap2-ΔChlo/pKD46 competent cells, and placed on LB plates contained three types of antibiotics, including kanamycin, tetracycline and chloramphenicol. After 48 h of electroporation, the positive bacterial colony is picked out and the bacmid DNA is extracted for PCR identification, and positive clones are screened for sequencing verification. The positive strain is named DH10Bac-Δ(Chia-Cath)-Cap2-ΔAc124-Rep2.

(2) The shuttle plasmid obtained in (1) and its corresponding recombinant bacmid comprising the baculovirus genome are used. The rAAV ITR-GOI carrying the heterologous functional gene fragment is integrated with the expression cassettes of the functional protein components necessary for assembly of the rAAV by using the shuttle plasmid and the recombinant bacmid obtained in (1). Thus, a recombinant bacmid comprising a BEV genome is obtained, which is capable of producing the rAAV.

BEV preparation method according to Bac-to-Bac system: the recombinant shuttle plasmid pFBD-(ITR-GOI) is transformed into E. coli DH10Bac-Δ(Chia-Cath)-Cap2-ΔAc124-Rep2 containing the corresponding recombinant bacmid using Tn7 transposon-mediated homologous recombination. As a result, E. coli DH10Bac-Tn7-(ITR-GOI-Δ(Chia-Cath)-Cap2-ΔAc124-Rep2 containing recombinant bacmids incorporating all rAAV packaging elements is obtained.

(3) The recombinant bacmid comprising the BEV genome producing the rAAV obtained in (2) is used to transfect a host cell line and cultured.

Figure 6B:
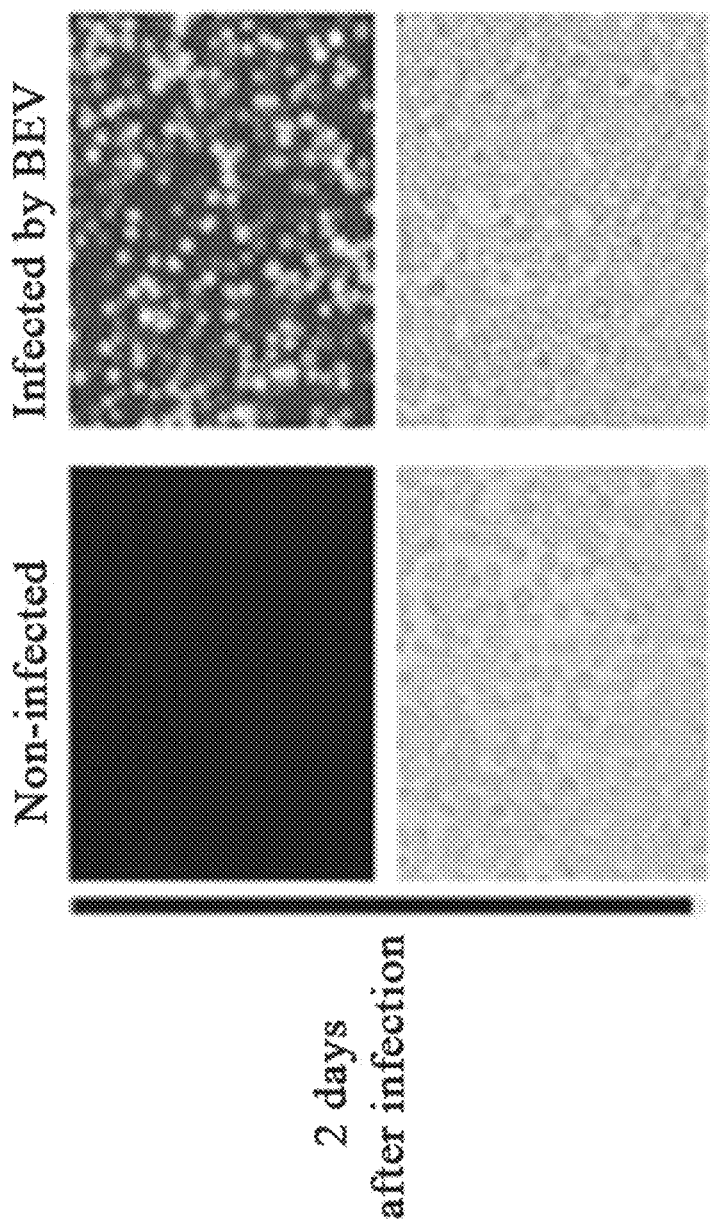

After the recombinant bacmid. DNA is extracted, it is used to transfect Sf9 insect cells to prepare BEV and rAAV. The transfected. Sf9 insect cells successfully produced BEV, and the Sf9 cells showed significant CPE. Significant expression of green fluorescent protein (GFP) is observed under fluorescence microscopy (FIG. 6B). The supernatant of the Sf9 cell culture in which CPE occurred is collected, which contained a large amount of BEV, that is, the first-generation BEV (P1). At the same time, Sf9 cells containing a large amount of rAAV are collected. For the method of preparing BEV (P2) by passage, refer to example 1.

Purification and virus characterization of rAAV produced by this system.

The rAAV prepared by BEV-infected Sf9 cells is purified (refer to the method step in Example 1). The experimental results showed that the Sf9 cells infected with BEV in this example had a rAAV yield of $2.80 \times 10^5$ VG per cell (FIG. 7).

Figure 6C:
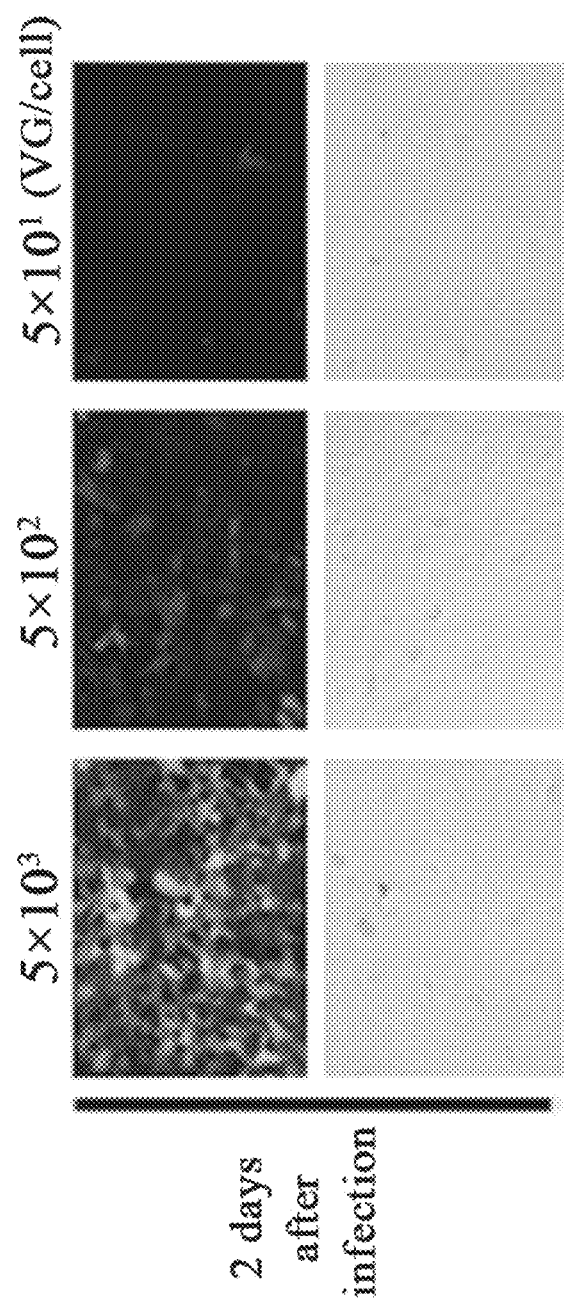

Purified rAAV is serially diluted to infect HEK293 cells cultured in 96-well plates. The expression of GFP is observed after 2 days post infection. The experimental results showed that the in vitro infection activity of rAAV prepared by the system is high (FIG. 6C).

Figure 6D:
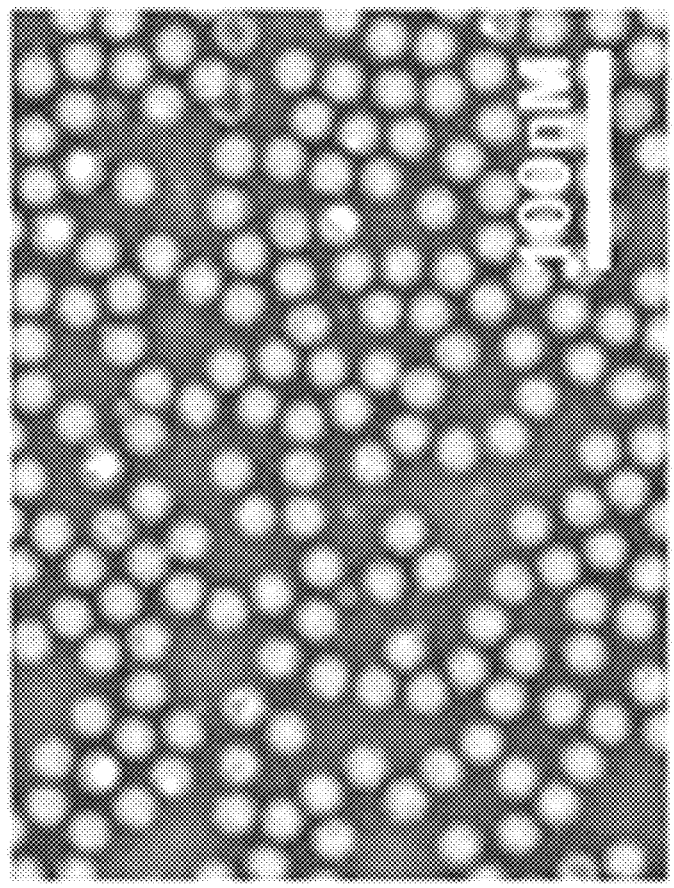

The morphology of the purified rAAV particles is observed using a transmission electron microscope. The solid intact rAAV particles are hexagonal uniform particles. The middle of hollow defective rAAV particles that do not carry nucleic acids is dyed dark. The statistical results of the electron micrographs show that the rAAV particles have a high integrity rate (FIG. 6D).

Figure 8F:
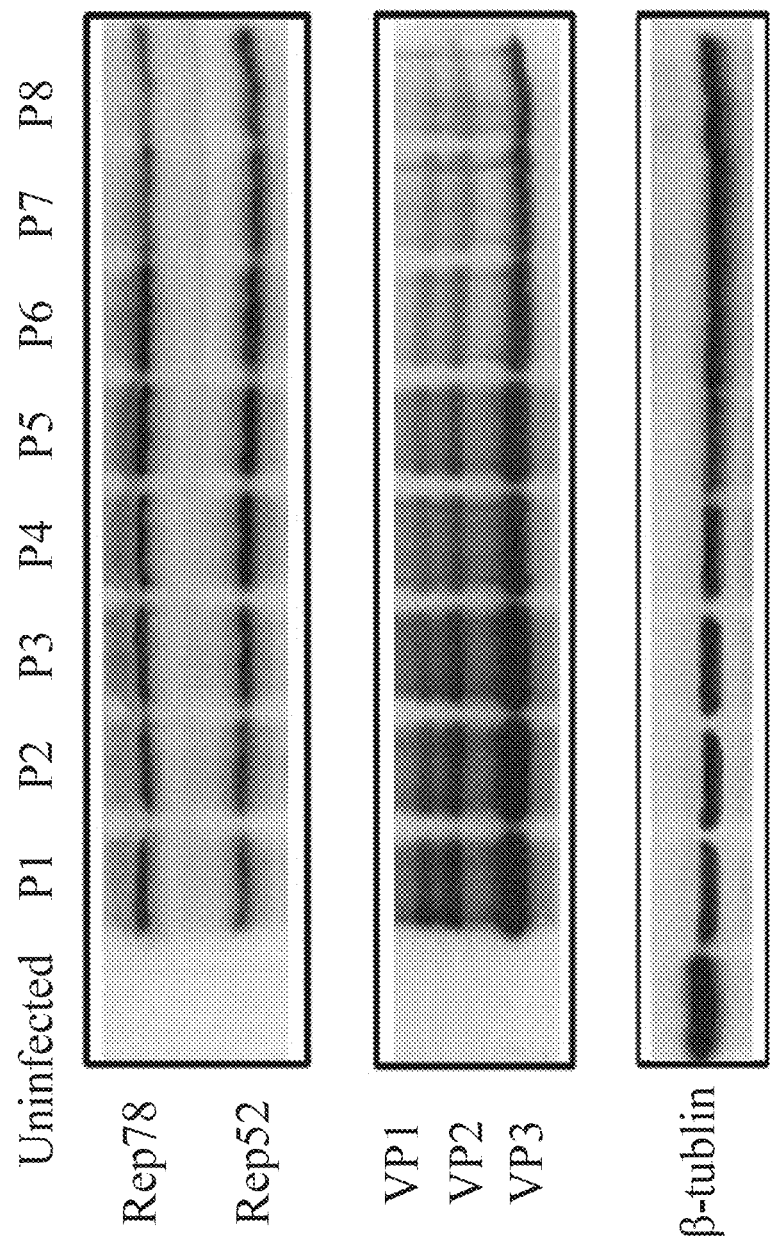

The BEV-Tn7-(ITR-GOI)-Δ(Chia-Cath)-Cap2-ΔAc124-Rep prepared in this example is subject to serial passage to infect Sf9 cells. The expression of Rep and Cap proteins is detected by Western blotting and the stability of BEV is tested. Compared with the OneBac system based on shuttle plasmid, the expression levels of Rep and Cap proteins in P1-P5 generation are higher, but gradually decreased after P5 generation, and the stability of BEV also decreased significantly after P5 generation (FIG. 8A). The BEV prepared in this example is stable at P1 to P8 generation in both Rep and Cap proteins expression levels (FIG. 8F). In summary, the stability of the BEV constructed in this example has been greatly improved.

It will be obvious to those skilled in the art that changes and modifications may be made, and therefore, the aim in the appended claims is to cover all such Changes and modifications.

What is claimed is:

1. A preparation system of rAAV, comprising a shuttle plasmid and a first recombinant bacmid; wherein:
   (i) the shuttle plasmid comprises an ITR-GOI, and an expression cassette of a Cap gene of AAV; and
   the first recombinant bacmid comprises a baculovirus genome having non-essential genes of Chia, and Cath absent, and an expression cassette of a Rep gene of AAV; wherein the expression cassette of the Rep gene of AAV is inserted into loci of the absent Chia and Cath genes;
   or
   (ii) the shuttle plasmid comprises the ITR-GOI, and an expression cassette of a Rep gene of AAV; and
   the first recombinant bacmid comprises a baculovirus genome having non-essential genes of Chia, and Cath absent, and an expression cassette of a Cap gene of AAV; wherein the expression cassette of the Cap gene of AAV is inserted into loci of the absent Chia and Cath genes.

2. A method of preparing a recombinant adeno-associated virus (rAAV), the method comprising:
   (1) introducing into a shuttle plasmid:
      (1a) a gene of interest flanked by inverted terminal repeats of AAV (ITR-GOI), and an expression cassette of a Cap gene of AAV; or
      (1b) the ITR-GOI, and an expression cassette of a Rep gene of AAV;
   (2) constructing a first recombinant bacmid through (2a) when the shuttle plasmid comprises (1a); or (2b) when the shuttle plasmid comprises (1b):
      (2a) deleting Chia and Cath genes from a genome of a wild-type bacmid, and inserting the expression cassette of the Rep gene of AAV into loci of the deleted Chia and Cath genes;
      (2b) deleting Chia and Cath genes from a genome of a wild-type bacmid, and inserting the expression cassette of the Cap gene of AAV into loci of the deleted Chia and Cath genes;
   (3) recombining the shuttle plasmid obtained from (1) with the first recombinant bacmid obtained from (2) to yield a second recombinant bacmid, the second recombinant bacmid comprising a recombinant baculovirus genome; and
   (4) transfecting a host cell line with the second recombinant bacmid obtained from (3) to prepare the rAAV.

3. The method of claim 2, wherein the expression cassette of the Rep gene of AAV or the expression cassette of the Cap gene of AAV in (2) are inserted by Red recombination.

4. The method of claim 2, wherein the shuttle plasmid is based on a pfast. Bac. Dual plasmid.

5. The method of claim 2, wherein the wild-type bacmid comprises a genome of baculovirus ACMNPY; and the expression cassette of the Rep gene of AAV or the expression cassette of the Cap gene of AAV in (2) are located downstream of and regulated by a P10 or a PH promoter.

6. The method of claim 2, wherein (3) comprises transforming the shuttle plasmid obtained from (1) into *Escherichia coli* comprising the first recombinant bacmid to yield *Escherichia coli* comprising the second recombinant bacmid, and extracting the second recombinant bacmid.

* * * * *

SEQUENCE LISTING

```
<160> NUMBER OF SEQ ID NOS: 10

<210> SEQ ID NO 1
<211> LENGTH: 23
<212> TYPE: DNA
<213> ORGANISM: Artificial Sequence
<220> FEATURE:
<223> OTHER INFORMATION: Fully synthetic
```

<400> SEQUENCE: 1
ttgttaaaaa acacacagct cgc                                           23

<210> SEQ ID NO 2
<211> LENGTH: 27
<212> TYPE: DNA
<213> ORGANISM: Artificial Sequence
<220> FEATURE:
<223> OTHER INFORMATION: Fully synthetic

<400> SEQUENCE: 2
aagcaatata ttgagtatca ttttagt                                       27

<210> SEQ ID NO 3
<211> LENGTH: 25
<212> TYPE: DNA
<213> ORGANISM: Artificial Sequence
<220> FEATURE:
<223> OTHER INFORMATION: Fully synthetic

<400> SEQUENCE: 3
tctcaacaca ctcgctattt ggaac                                         25

<210> SEQ ID NO 4
<211> LENGTH: 24
<212> TYPE: DNA
<213> ORGANISM: Artificial Sequence
<220> FEATURE:
<223> OTHER INFORMATION: Fully synthetic

<400> SEQUENCE: 4
ttccatggct gaaggcgaat tggc                                          24

<210> SEQ ID NO 5
<211> LENGTH: 29
<212> TYPE: DNA
<213> ORGANISM: Artificial Sequence
<220> FEATURE:
<223> OTHER INFORMATION: Fully synthetic

<400> SEQUENCE: 5
aacttgctaa tataaaagcc aaaatccgc                                     29

<210> SEQ ID NO 6
<211> LENGTH: 28
<212> TYPE: DNA
<213> ORGANISM: Artificial Sequence
<220> FEATURE:
<223> OTHER INFORMATION: Fully synthetic

<400> SEQUENCE: 6
ttttaattct tatatcagtg cacggttc                                      28

<210> SEQ ID NO 7
<211> LENGTH: 33
<212> TYPE: DNA
<213> ORGANISM: Artificial Sequence
<220> FEATURE:
<223> OTHER INFORMATION: Fully synthetic

<400> SEQUENCE: 7
tttataaaaa tgttttttat tctttcacaa ttc                                33

<210> SEQ ID NO 8

```
<211> LENGTH: 24
<212> TYPE: DNA
<213> ORGANISM: Artificial Sequence
<220> FEATURE:
<223> OTHER INFORMATION: Fully synthetic

<400> SEQUENCE: 8
acgttgaatt ggccgttacc attg                                              24

<210> SEQ ID NO 9
<211> LENGTH: 24
<212> TYPE: DNA
<213> ORGANISM: Artificial Sequence
<220> FEATURE:
<223> OTHER INFORMATION: Fully synthetic

<400> SEQUENCE: 9
gtgtaggctg gagctgcttc gaag                                              24

<210> SEQ ID NO 10
<211> LENGTH: 31
<212> TYPE: DNA
<213> ORGANISM: Artificial Sequence
<220> FEATURE:
<223> OTHER INFORMATION: Fully synthetic

<400> SEQUENCE: 10
atgggaatta gccatggtcc atatgaatat c                                      31
```